(12) United States Patent
Gomez et al.

(10) Patent No.: US 11,974,827 B2
(45) Date of Patent: May 7, 2024

(54) ASSOCIATION PROCESSES AND RELATED SYSTEMS FOR MANIPULATORS

(71) Applicant: Intuitive Surgical Operations, Inc., Sunnyvale, CA (US)

(72) Inventors: Daniel H. Gomez, Los Gatos, CA (US); Ian E. McDowall, Woodside, CA (US); Govinda Payyavula, Fremont, CA (US); John Ryan Steger, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 579 days.

(21) Appl. No.: 16/633,501

(22) PCT Filed: Jul. 18, 2018

(86) PCT No.: PCT/US2018/042641
§ 371 (c)(1),
(2) Date: Jan. 23, 2020

(87) PCT Pub. No.: WO2019/023014
PCT Pub. Date: Jan. 31, 2019

(65) Prior Publication Data
US 2021/0401519 A1    Dec. 30, 2021

Related U.S. Application Data

(60) Provisional application No. 62/551,700, filed on Aug. 29, 2017, provisional application No. 62/537,782, filed on Jul. 27, 2017.

(51) Int. Cl.
*A61B 34/37*    (2016.01)
*A61B 34/00*    (2016.01)
(Continued)

(52) U.S. Cl.
CPC .............. *A61B 34/37* (2016.02); *A61B 34/20* (2016.02); *A61B 34/74* (2016.02); *A61B 34/76* (2016.02);
(Continued)

(58) Field of Classification Search
CPC .... A61B 2034/2048; A61B 2034/2059; A61B 2034/742; A61B 2090/065;
(Continued)

(56) References Cited

U.S. PATENT DOCUMENTS 6,459,926 B1    10/2002    Nowlin et al.
2002/0128552 A1    9/2002    Nowlin et al.
(Continued)

FOREIGN PATENT DOCUMENTS

| GB | 2560390 A | 9/2018 |
|---|---|---|
| WO | WO-2011143338 A1 | 11/2011 |
| WO | WO-2014151621 A1 | 9/2014 |

OTHER PUBLICATIONS

Fernandez (ROS Package Summary for twist_mux, Nov. 13, 2014), available at http://wiki.ros.org/twist_mux (Year: 2014).*
(Continued)

*Primary Examiner* — Scott Luan
(74) *Attorney, Agent, or Firm* — MARSHALL, GERSTEIN & BORUN LLP

(57) ABSTRACT

A computer-assisted medical system includes robotic manipulators, a user input system operable to generate signals to control the manipulators, and a controller configured to execute instructions to perform operations. A portion of the user input system is movable relative to the plurality of manipulators. The operations include, in a pairing mode, associating a first manipulator of the plurality of manipulators with the portion of the user input system based on movement of the portion of the user input system relative to (Continued)

the first manipulator, and, in a following mode, controlling motion of the first manipulator in accordance with an indication generated by the user input system in response to operation of the portion of the user input system by a user.

26 Claims, 14 Drawing Sheets

(51) Int. Cl.
*A61B 34/20* (2016.01)
*A61B 90/00* (2016.01)
*H04W 12/50* (2021.01)

(52) U.S. Cl.
CPC .............. *A61B 90/06* (2016.02); *A61B 90/37* (2016.02); *H04W 12/50* (2021.01); *A61B 2034/2048* (2016.02); *A61B 2034/2059* (2016.02); *A61B 2090/065* (2016.02)

(58) Field of Classification Search
CPC ... A61B 2090/571; A61B 34/20; A61B 34/30; A61B 34/32; A61B 34/37; A61B 34/74; A61B 34/76; A61B 90/06; A61B 90/361; A61B 90/03
See application file for complete search history.

(56) References Cited

U.S. PATENT DOCUMENTS

| | | |
|---|---|---|
| 2003/0216715 A1 | 11/2003 | Moll et al. |
| 2007/0003061 A1 | 1/2007 | Jung et al. |
| 2009/0036902 A1 | 2/2009 | Dimaio et al. |
| 2009/0253109 A1 | 10/2009 | Anvari et al. |
| 2010/0291520 A1* | 11/2010 | Kurenov ............ A61B 17/0491 434/262 |
| 2011/0137322 A1* | 6/2011 | Moll ................... G09B 23/285 606/130 |
| 2011/0144806 A1 | 6/2011 | Sandhu et al. |
| 2011/0276058 A1 | 11/2011 | Choi et al. |
| 2014/0055489 A1 | 2/2014 | Itkowitz et al. |
| 2016/0094934 A1 | 3/2016 | Yang et al. |
| 2016/0249992 A1 | 9/2016 | Ruiz Morales et al. |
| 2016/0338786 A1 | 11/2016 | Robinson et al. |
| 2017/0035521 A1 | 2/2017 | Diolaiti et al. |
| 2017/0038837 A1 | 2/2017 | Faaborg et al. |
| 2020/0222129 A1 | 7/2020 | Gomez et al. |

OTHER PUBLICATIONS

Extended European Search Report for Application No. EP18838547 dated Jun. 16, 2020, 14 pages.
Laser Corporation: "NFC pairing video", Aug. 16, 2018, p. 1, XP054980512, Retrieved from the Internet: URL: https://www.youtube.com/watch?v=HyhgalCoB98 [retrieved on Jun. 2, 2020].
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Search Report and Written Opinion in related International Application Serial No. PCT/US208/042641, dated Dec. 17, 2018, 17 pages.
Extended European Search Report for Application No. EP18837858.2 mailed on Jun. 3, 2020, 12 pages.
International Search Report and Written Opinion for Application No. PCT/US2018/042690, mailed on Dec. 17, 2018, 19 pages.
Anonymous: "GazePointer download|SourceForge.net" Nov. 2016, pp. 3 Pages, XP093085718, Retrieved from the Internet: URL:https://web.archive.org/web/20161111072632/https://sourceforge.net/projects/gazepointer/.
Extended European Search Report for Application No. EP23182209.9, mailed on Oct. 9, 2023, 10 pages.

* cited by examiner

ASSOCIATION PROCESSES AND RELATED SYSTEMS FOR MANIPULATORS

CROSS-REFERENCE TO RELATED APPLICATIONS

This application is a U.S. National Stage Application under 35 U.S.C. § 371 and claims the benefit of International Patent Application Serial No. PCT/US2018/042641, filed on Jul. 18, 2018 which claims the benefit of and priority to U.S. Provisional Patent Application No. 62/537,782, filed on Jul. 27, 2017 and U.S. Provisional Patent Application No. 62/551,700, filed on Aug. 29, 2017. The entire contents of each of the foregoing applications are hereby incorporated by reference.

TECHNICAL FIELD

This specification relates to association processes and related systems for manipulators, for example, for teleoperated manipulators.

BACKGROUND

Robotic manipulators can be operated to control motion of instruments in a workspace. For example, such manipulators can be used to perform non-medical and medical procedures. As a specific example, teleoperated manipulators can be used to perform minimally invasive surgical procedures. An operator can control the manipulators using a user control system, e.g., connected wirelessly or via a wired connection to the teleoperated manipulators. The user control system can include multiple user input devices such that each of the teleoperated manipulators can be controlled by a distinct user input device of the user control system. The operator can thus independently control each of the teleoperated manipulators using the user input devices.

SUMMARY

In one aspect, a computer-assisted medical system includes teleoperated manipulators, a user input system operable to generate signals to control the manipulators, and a controller configured to execute instructions to perform operations. A portion of the user input system is movable relative to the plurality of manipulators. The operations include, in a pairing mode, associating a first manipulator of the plurality of manipulators with the portion of the user input system based on movement of the portion of the user input system relative to the first manipulator, and, in a following mode, controlling motion of the first manipulator in accordance with an indication generated by the user input system in response to operation of the portion of the user input system by a user.

In another aspect, a method of operating a computer-assisted medical system including a plurality of teleoperated manipulators is featured. The method includes, in a pairing mode, associating a first manipulator of the plurality of manipulators with a portion of a user input system based on movement of the portion of the user input system relative to the first manipulator, and, in a following mode, controlling motion of the first manipulator in accordance with an indication generated by the user input system in response to operation of the portion of the user input system by a user.

In another aspect, a computer-assisted medical system includes teleoperated manipulators, an optical motion detection system operable to generate signals to control the plurality of manipulators, and a controller configured to execute instructions to perform operations. The optical motion detection system is configured to detect motion of hands of a user. The operations include, in a pairing mode, associating a first manipulator of the plurality of manipulators with a first hand of the user based on movement of the first hand relative to the first manipulator, and, in a following mode, controlling motion of the first manipulator in accordance with an indication generated by the optical motion detection system in response to movement of the first hand of the user.

Advantages of the foregoing may include, but are not limited to, those described below and herein elsewhere. For example, associations between portions of the user input system (e.g. one or more user input devices) and the teleoperated manipulators can be formed in an intuitive manner for the operator. Rather than having to interact with lists and information presented on a display that do not provide the operator with an intuitive sense of relative poses of the teleoperated manipulators, an operator can initiate association between a user input device and a particular teleoperated manipulator through physical manipulation of the user input device in an intuitive manner. During the pairing mode, the operator can physically move the user input device relative to the teleoperated manipulators to select a manipulator of the teleoperated manipulators to associate with the user input device. For example, the user input device can be moved toward or to a position proximate a manipulator to which the user input device is to be associated. This process provides an intuitive way for the operator to associate the user input device.

Human-detectable feedback can be provided during the pairing mode so that the operator can be kept apprised of states and processes of devices, e.g., the user input devices and the manipulators. For example, the controller can generate feedback indicative of association states of the portions of the user input system or association states of the manipulators. Based on the feedback, the operator can initiate association processes for the portions of the user input system that have not already been associated, the manipulators that have not already been associated, or both. In some implementations, the controller can generate feedback indicative of a proposed association prior to finalizing an association between a user input device and a manipulator. This can enable the operator to make adjustments to a proposed association, thereby providing the operator with greater control during the association process. In some implementations, human-detectable feedback can be continued or newly provided after an association has been made, and indicate the portion of the user input system that is associated with a particular manipulator, and vice versa. Further, the controller can disassociate a user input device or a manipulator in response to user input or a system event.

Although some of the examples described herein often refer to medical procedures and medical instruments, the techniques disclosed also apply to non-medical procedures and non-medical instruments. For example, the instruments, systems, and methods described herein may be used for non-medical purposes including industrial uses, general robotic uses, manipulation of non-tissue work pieces, and/or cosmetic improvements. Other non-surgical applications include use on tissue removed from human or animal anatomies (without return to a human or animal anatomy) or on human or animal cadavers.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Example Systems

Figure 1:
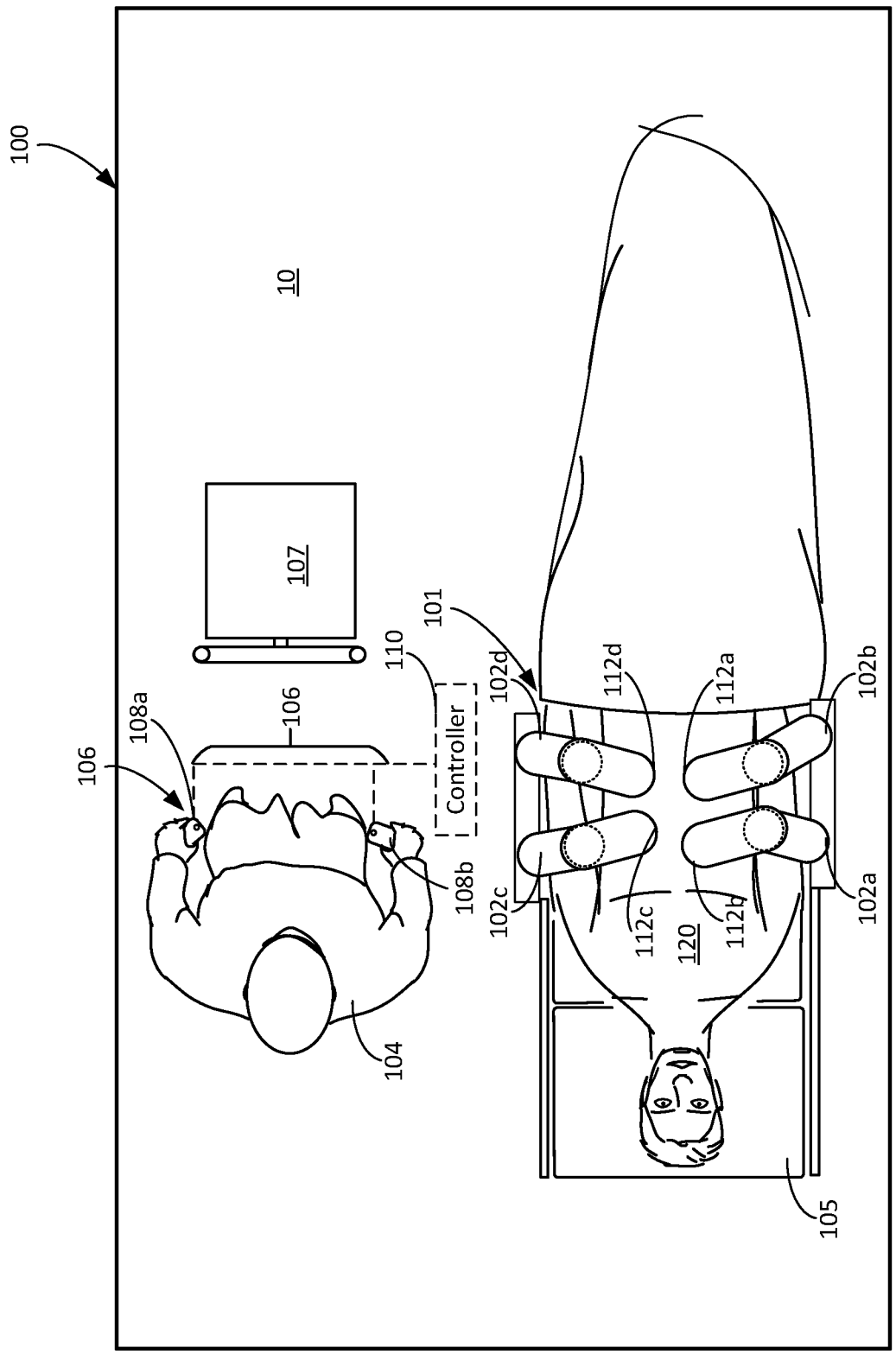
FIG. 1 is a top view of a system including a manipulator.

Referring to FIG. 1, a system 100 in an environment 10 includes a manipulator system 101 including manipulators 102a, 102b, 102c, 102d (collectively referred to as manipulators 102) that can be teleoperated by an operator 104. The manipulators 102 are termed "teleoperated manipulators" because they that can be teleoperated by an operator 104 through a physically separate user input system 106. In some implementations, the manipulators 102 can also be controlled directly through manual interaction with the manipulators 102 themselves. Thus, "teleoperated manipulators" as used in this application include manipulators that can be controlled only through teleoperation, and manipulators that can be controlled through teleoperation and through direct manual control. The manipulators 102 include movable portions that can support instruments (not shown), e.g., surgical and medical instruments. The movable portions, for example, correspond to distal ends 112a, 112b, 112c, 112d of the manipulators 102. When the system 100 is operated in a following mode, the operator 104 can operate a user input system 106 to control motion of the manipulators 102.

The operator can view a display system 107 that presents imagery representing the instruments mounted on the manipulators 102 while the manipulators 102 are being controlled by the operator 104. For example, an instrument including an image capture device such as a camera is mounted to one of the manipulators 102. The image capture device generates imagery of the distal ends of other instruments mounted to the other manipulators 102 so that the operator 104 can monitor poses of the distal ends of the instruments during a surgical operation.

The user input system 106 is connected to the manipulators 102, e.g., wirelessly or using a wired connected. The user input system 106 includes multiple distinct portions movable relative to the manipulators 102 and operable for controlling operations of the manipulators 102. For example, the user input system 106 includes user input devices 108a, 108b (collectively referred to as user input devices 108) movable relative to the manipulators 102. The user input system 106 can include other user input devices, e.g., keyboards, touchscreens, buttons, foot pedals, etc., in addition to the user input devices 108 used to control movement of the manipulators 102 in the following mode. These other user input devices can be used to control the display system 107 and otherwise control operations of the system 100.

As described herein, in response to movement of the user input devices 108 in a pairing mode, a controller 110 of the system 100 can associate a user input device of the user input system 106 with a corresponding one of the manipulators 102 during an association process. When associated, the user input device can be operated to control the corresponding manipulator in the following mode to perform an operation, e.g., a medical operation, a surgical operation, a diagnostic operation, etc.

Figure 2:
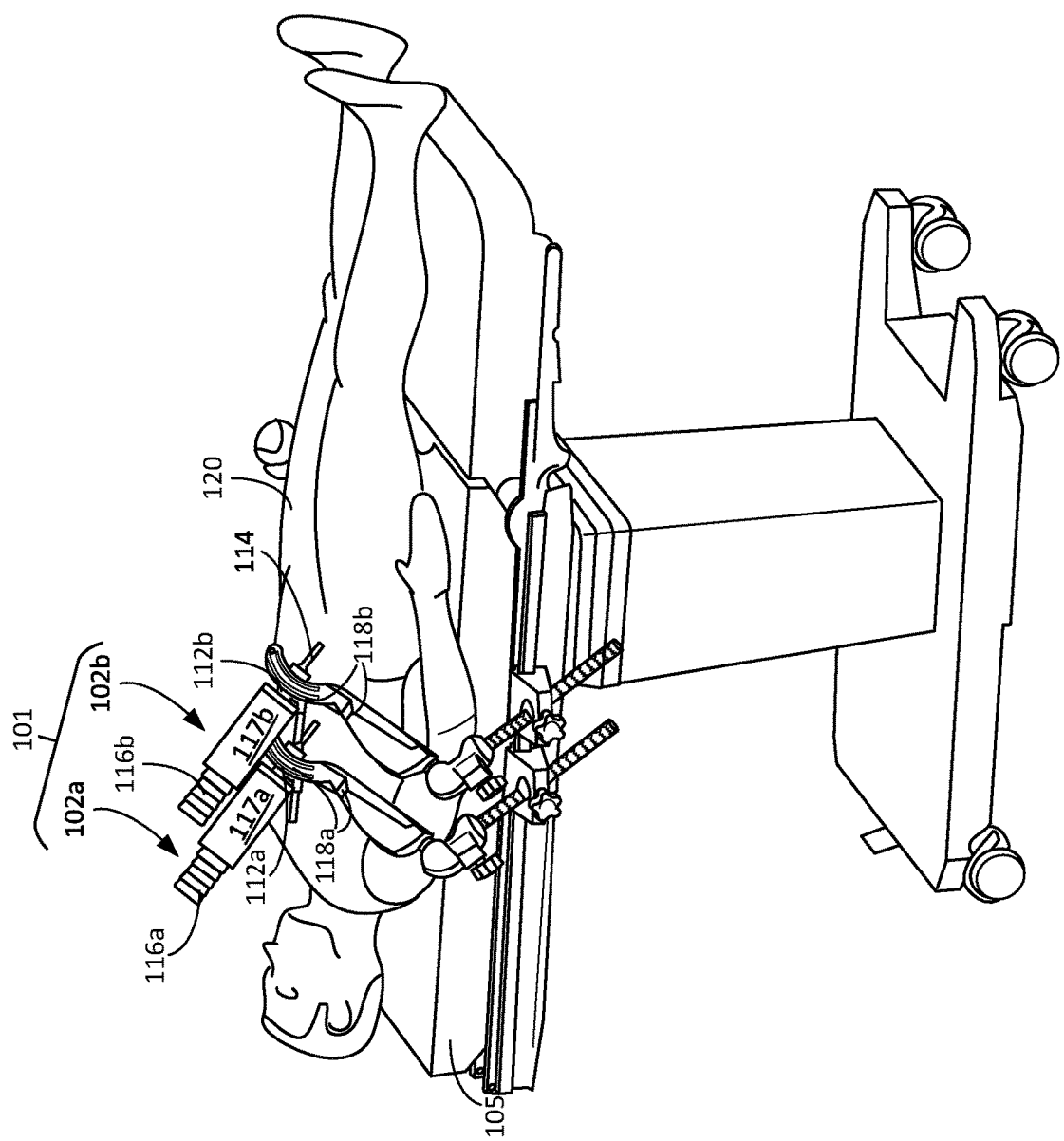
FIG. 2 is a front perspective view of a manipulator and a patient on an operating table.

FIG. 2 shows an example of the manipulator system 101. For simplicity, only the manipulators 102a, 102b of the manipulator system 101 are shown. In some implementations, the manipulator system 101 includes a single manipulators or includes three or more manipulators, e.g., four manipulators 102a, 102b, 102c, 102d as depicted in FIG. 1. In addition, although FIG. 2 is described with respect to the manipulators 102a, 102b, the manipulators 102c, 102d of FIG. 1 can include features similar to those presented with respect to the manipulators 102a, 102b. The manipulators 102a, 102b, 102c, 102d may differ in that different instruments may be mounted to the manipulators 102a, 102b, 102c, 102d, and in that the manipulators 102a, 102b, 102c, 102 may be supported by an operating table 105 at different locations along the operating table 105.

The manipulators 102a, 102b include portions movable about a workspace 114. For example, these portions can correspond to distal ends 112a, 112b of the manipulators 102a, 102b that are movable about the workspace 114. The distal ends 112a, 112b support instruments 116a, 116b such that the instruments 116a, 116b can be moved about the workspace when the distal ends 112a, 112b are moved about the workspace 114. In some implementations, actuation modules 117a, 117b are supportable at the distal ends 112a, 112b of the manipulators 102a, 102b. The actuation modules 117a, 117b are removably mounted to the distal ends 112a, 112b of the manipulators 102a, 102b and include one or more actuators operable to generate insertion and roll motions of the instruments 116a, 116b. The instruments 116a, 116b are insertable through the actuation modules 117a, 117b such that the instruments 116a, 116b are attached to the actuation modules 117a, 117b, which in turn are attached to the distal ends 112a, 112b of the manipulators 102a, 102b.

The manipulators 102a, 102b include powered joints 118a, 118b that can be driven to move the distal ends 112a, 112b of the manipulators 102a, 102b about the workspace 114. Each of the manipulators 102a, 102b includes multiple powered joints 118a, 118b that enable motion of the distal ends 112a, 112b in multiple degrees of freedom, e.g., pitch, yaw, and roll motions of the distal ends 112a, 112b of the manipulators 102a, 102b. The instruments and manipulators described herein can have one or more degrees of freedom that vary in implementations. For example, the one or more degrees of freedom include one or more of a yaw motion of the distal portion of the manipulator, a pitch motion of the distal portion of the manipulator, an insertion motion of the instrument supported by the manipulator, a roll motion of the instrument, a yaw motion of the end effector of the instrument, a wrist motion of an end effector of the instrument, or a jaw or grip motion of the end effector of the instrument.

The system 100 is a computer-assisted system. For example, the controller 110 can control operation of the system 100 or operations of portions of the system 100. In some examples, the controller 110 can control operation of the actuators of the powered joints 118a, 118b. In this regard, the distal ends 112a, 112b of the manipulators 102a, 102b, and hence the instruments 116a, 116b, can be moved about the workspace 114 when the user input devices 108 (shown in FIG. 1) are operated by the operator 104. In a following mode, a follower of a manipulator moves in response to movement of a leader. The movement of the follower can emulate the movement of the leader. For a particular manipulator for example, the leader can be one or more of the user input devices 108, and the follower can be one or more components of the manipulator. The follower can be an end effector of the manipulator, a remote center of the manipulator, or some other component of the manipulator. In some examples, in the following mode, the distal ends 112a, 112b are the followers. For example, actuators of the powered joints 118a, 118b can be controlled to generate motion of links of the manipulators 102a, 102b about the powered joints 118a, 118b, thereby repositioning the distal ends 112a, 112b of the manipulators 102a, 102b. The motions of the distal ends 112a, 112b emulate the motions of the user input devices 108. In other examples, the motion of the user input devices 108 in the following mode can cause an instrument mounted to the distal end 112a or 112b to be ejected from the distal end 112a or 112b.

Referring to both FIGS. 1 and 2, in some implementations, the system 100 is a medical system to perform a medical procedure on a patient 120. For example, the system 100 is a diagnostic system that can be used to perform diagnostics on the patient 120. Alternatively or additionally, the system 100 is a surgical system that can be used to perform a surgical operation on the patient 120.

A variety of alternative computer-assisted teleoperated instruments 116a, 116b can be used. For example, the teleoperated instruments 116a, 116b can be surgical instruments of different types having differing end effectors. In some cases, the instruments 116a, 116b include multiple DOFs such as, but not limited to, roll, pitch, yaw, insertion depth, opening/closing of jaws, actuation of staple delivery, activation of electro-cautery, and the like. Motion in at least some of such DOFs can be generated by the actuation modules 117a, 117b of the manipulators 102a, 102b to which the instruments 116a, 116b are selectively coupled.

If the instruments 116a, 116b are medical or surgical instruments, possible end effectors include, for example, DeBakey Forceps, microforceps, and Potts scissors include first and second end effector elements that pivot relative to each other so as to define a pair of end effector jaws. Other end effectors, including scalpels and electrocautery probes, have a single end effector element. For instruments having end effector jaws, the jaws will often be actuated by squeezing the grip members of input devices. In some cases, one or more of the instruments 116a, 116b includes an image capture device, such as a camera. The image capture device can capture imagery of other instruments in the workspace, and this imagery can be presented to the operator 104 to allow the operator 104 to visually monitor positions of other instruments in the workspace.

Figure 3A:
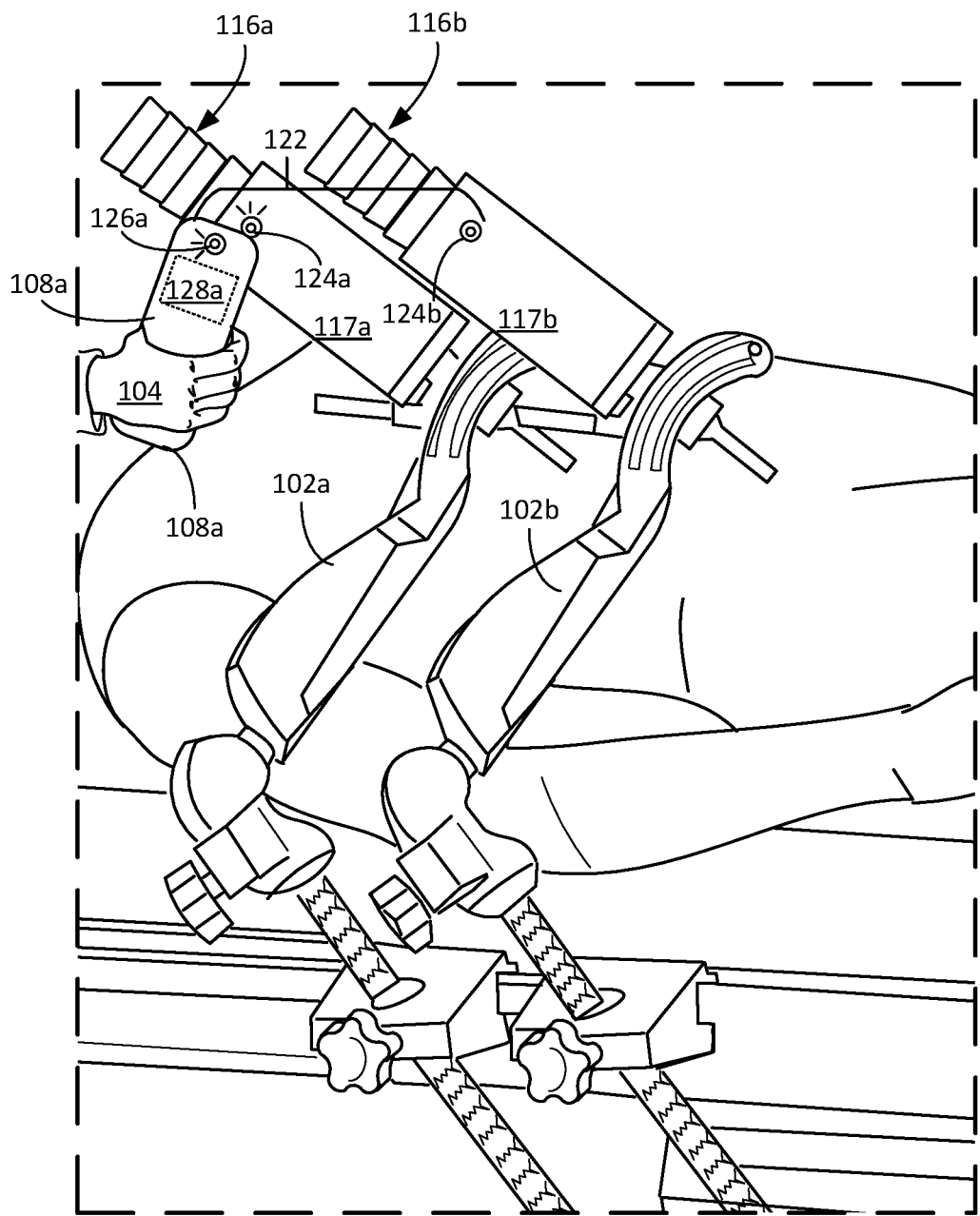
FIGS. 3A and 3B illustrate a process to associate user input devices with manipulators.
Figure 3B:
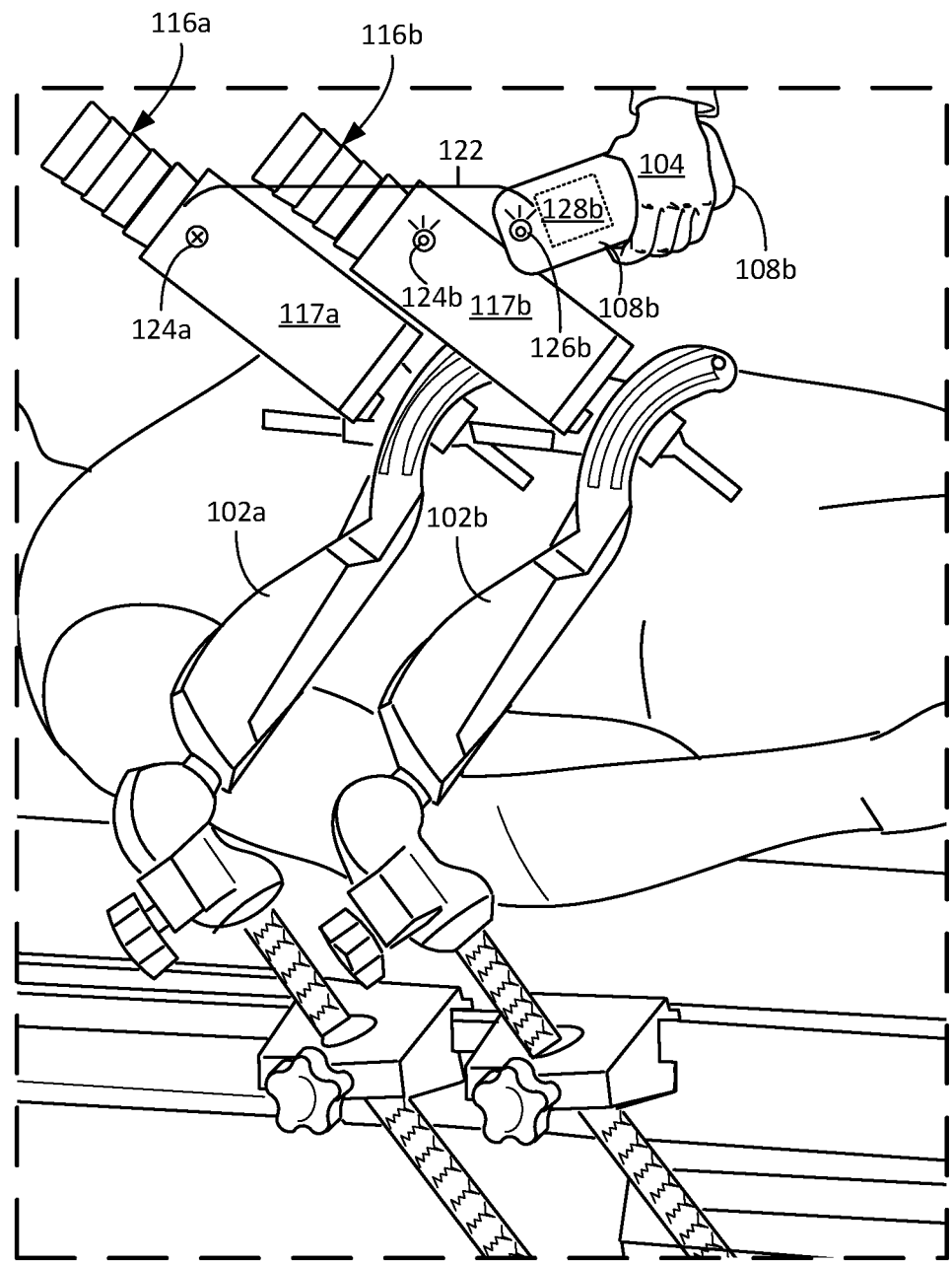

As depicted in FIGS. 3A and 3B, the system 100 includes an indicator system 122. The indicator system 122 includes one or more indicator devices to generate human-perceptible indications to provide feedback to the operator 104 during the association process or during the following mode. For example, the indicator system 122 includes indicator devices 124a, 124b. The indicator device 124a provides human-perceptible indications originating in the vicinity of the manipulator 102a, and the indicator device 124b provides human-perceptible indications originating in the vicinity of the manipulator 102b. The indicator devices 124a, 124b can be attached to, positioned on, or positioned proximate to the manipulators 102a, 102b, respectively. The indicator devices 124a, 124b can be located on the actuation modules 117a, 117b and thus can be attached to the manipulators 102a, 102b through the actuation modules 117a, 117b. Alternatively, in some implementations, the indicator devices 124a, 124b are directly attached to or positioned on the manipulators 102a, 102b.

The indicator system 122 further includes an indicator device 126a (on the user input device 108a shown in FIG. 3A) and an indicator device 126b (on the user input device 108b shown in FIG. 3B). The indicator device 126a provides human-perceptible indications originating in the vicinity of the user input device 108a, and the indicator device 126b provides human-perceptible indications originating in the vicinity of the user input device 108b. For example, the indicator devices 126a, 126b are attached to, positioned on, or positioned proximate to the user input devices 108a, 108b, respectively.

If the indicator devices 124a, 124b, 126a, 126b provide visual feedback, the indicator devices 124a, 124b, 126a, 126b each includes an appropriate visual feedback device. Example visual feedback devices include light-emitting diodes or other light sources, electronic displays such as LCD or OLED displays, etc. In some implementations, the indicator devices 124a, 124b, 126a, 126b emit different colors of light to intuitively indicate to the operator the statuses of the user input devices 108a, 108b and the manipulators 102a, 102b. In some implementations, the indicator devices 124a, 124b, 126a, 126b present different numeric, textual, or graphical patterns to indicate to the operator the statuses of the user input devices 108a, 108b and the manipulators 102a, 102b. For example, when the pairing mode is initiated, a green light or a flashing "O" can indicate that a device is in an unassociated state, and a red light or a steadily presented (not flashing) "O" can indicate that a device is in an associated state, or vice versa. In some cases, as described herein, a yellow light or a flashing or steadily presented "X" can provide a visual warning, such as to the operator 104.

In some implementations, the indicator devices 124a, 124b, 126a, 126b can provide visual feedback for indicating additional information about the statuses of the user input devices 108a, 108b and the manipulators 102a, 102b. In some implementations, the indicator devices 124a, 124b, 126a, 126b present visual feedback to indicate which user input device recommended to be associated with which manipulator, or to indicate which user input device will be associated with which manipulator upon confirmation. As one example, where the user input device 108a and the manipulator 102a is recommended to be associated with each other, or will be associated with which manipulator upon confirmation, both the user input device 108a and the manipulator 102*a* can flash matching, similar, or identical: color, number, text, graphics, flashing sequence, or other visual feedback.

In some implementations, the indicator devices 124*a*, 124*b*, 126*a*, 126*b* present visual feedback to indicate which user input device has been, or is currently, associated with which manipulator. As one example, after the user input device 108*a* is associated with the manipulator 102*a*, both the user input device 108*a* and the manipulator 102*a* can steadily present (not flashing) similar or identical: color, number, text, graphical pattern, or other visual feedback. In various implementations, this steady presentation of color, number, text, graphics, or other textual feedback can last for the entire duration during which the user input device 108*a* is associated with the manipulator 102*a*.

In addition to or as an alternative to providing visual feedback, the indicator devices 124*a*, 124*b*, 126*a*, 126*b* can provide human-perceptible tactile feedback, aural feedback, or a combination thereof. If the indicator devices 124*a*, 124*b*, 126*a*, 126*b* provide tactile feedback, the tactile feedback can include vibro-tactile feedback, force feedback, or other forms of feedback associated with a user's sense of touch. The indicator devices 124*a*, 124*b*, 126*a*, 126*b* can include, for example, a vibration generator. For example, the indicator devices 126*a*, 126*b* can generate vibrations that serve as haptic feedback for the operator 104 when the operator 104 is holding the user input devices 108*a*, 108*b*. If the indicator devices 124*a*, 124*b*, 126*a*, 126*b* provide aural feedback, the indicator devices 124*a*, 124*b*, 126*a*, 126*b* include, for example, an audio output device such a speaker. In such cases, the indicator devices 124*a*, 124*b*, 126*a*, 126*b* can narrate audible feedback to the operator 104.

As noted above, the feedback provided by the indicator devices 124*a*, 124*b*, 126*a*, 126*b* can be indicative of statuses of the manipulators 102*a*, 102*b* and the user input devices 108*a*, 108*b* before, during, and after the association process. For example, the feedback can be indicative of association states of the manipulators 102*a*, 102*b*, association states of the user input devices 108*a*, 108*b*, or both. An association state can be indicative of whether a particular manipulator is associated with a user input device or whether a particular user input device is associated with a manipulator.

Alternatively or additionally, the indicator devices 124*a*, 124*b*, 126*a*, 126*b* can provide feedback during an association process to provide the operator 104 with information pertaining to the association process. The feedback can be indicative of a proposed association between a user input device and a manipulator. For example, as described herein, the operator 104 can operate the user input devices 108*a*, 108*b* to propose an association between a particular user input device and a particular manipulator, and the indicator devices 124*a*, 124*b*, 126*a*, 126*b* can provide feedback indicative of this proposed association. In some implementations, the feedback can be indicative of a usable or an optimal association between a user input device and a manipulator. For example, as described herein with respect to FIGS. 8A and 8B, the controller 110 (shown in FIG. 1) can determine usable or optimal associations between the user input devices 108 and the manipulators 102 and provide a signal indicative of the usable or optimal associations.

As shown in FIG. 3A, the user input device 108*a* can further include a sensor 128*a* that can indicate, to the controller 110 (shown in FIG. 1), movement of the user input device 108*a*. For example, the sensor 128*a* can indicate, e.g., generate a signal indicative of, a relative movement between the user input device 108*a* and the manipulators 102. The controller 110, during the pairing mode, can associate a particular manipulator with the user input device 108*a* in response to the relative movement between the user input device 108*a* and the particular manipulator satisfying an association condition.

Similarly, as shown in FIG. 3B, the user input device 108*b* can further include a sensor 128*b* that can indicate, to the controller 110 (shown in FIG. 1), movement of the user input device 108*b*. For example, the sensor 128*b* can indicate, e.g., generate a signal indicative of, a relative movement between the user input device 108*b* and the manipulators 102. The controller 110, during the pairing mode, can associate a particular manipulator with the user input device 108*b* in response to the relative movement between the user input device 108*b* and the particular manipulator satisfying an association condition. Examples of association conditions are described with respect to the process illustrated in FIG. 7.

FIGS. 3A and 3B illustrate an example of manual operation of the user input devices 108*a*, 108*b* to associate the user input devices 108*a*, 108*b* with the manipulators 102*a*, 102*b*. As shown in FIG. 3A, if the manipulators 102*a*, 102*b* were not previously associated with a user input device, the indicator devices 124*a*, 124*b* both provide feedback indicating that the manipulators 102*a*, 102*b* are in unassociated states. Similarly, the indicator device 126*a* also provides feedback indicating that the user input device 108*a* was not previously associated with a manipulator.

To initiate the association between the user input device 108*a* and the manipulator 102*a*, in a pairing mode, the user input device 108*a* is moved relative to the manipulator 102*a*. For example, the user input device 108*a* is moved to a region proximate the manipulator 102*a*. Based on this movement of the user input device 108*a* relative to the manipulator 102*a*, the controller 110 (shown in FIG. 1) associates the manipulator 102*a* with the user input device 108*a*.

The controller 110 can control the indicator devices 124*a*, 126*a* to provide human-perceptible feedback indicating that the movement of the user input device 108*a* relative to the manipulator 102*a* corresponds to a proposed association between the user input device 108*a* and the manipulator 102*a*. For example, both the indicator device 124*a* and the indicator device 126*a* can provide matching, similar, or identical feedback so that the operator 104 can intuitively understand that the proposed association is between the user input device 108*a* and the manipulator 102*a* (and, e.g., not between the user input device 108*a* and the manipulator 102*b*). In some cases, this feedback is provided as the operator 104 moves the user input device 108*a*. As a result, the operator 104 is able to easily determine when the user input device 108*a* has been appropriately moved to satisfy the association condition to associate the user input device 108*a* and the manipulator 102*a* (and, e.g., to not satisfy the association condition to associate the user input device 108*a* and the manipulator 102*b*). As described with respect to the process illustrated in FIG. 7, in some cases, the operator 104 provides confirmation of the proposed association so that the controller 110 proceeds with associating the manipulator 102*a* with the user input device 108*a*. In some implementations, the indicator devices 124*a*, 126*a* can indicate, after the association is made, that the user input device 108*a* is associated with the manipulator 102*a*. For example, the indicator devices 124*a*, 126*a* provide matching, similar, or identical feedback for part or the entire duration that the user input device 108*a* is associated with the manipulator 102*a*. As one example, the indicator devices 124*a*, 126*a* can provide the same color, number, text, graphic, or other visual feedback for the entire duration that the user input device 108a is associated with the manipulator 102a.

Referring to FIG. 3B, in a pairing mode, the user input device 108b is moved relative to the manipulator 102b. For example, the user input device 108b is moved to a region proximate the manipulator 102b. Based on this movement of the user input device 108b relative to the manipulator 102b, the controller 110 (shown in FIG. 1) associates the manipulator 102b with the user input device 108b. As described herein, the user input device 108b associated with the manipulator 102b is distinct from the user input device 108a associated with the manipulator 102a so that the manipulators 102a, 102b can be independently controlled using the user input devices 108a, 108b of the user input system 106.

The controller 110 can control the indicator devices 124b, 126b to provide human-perceptible feedback indicating that the movement of the user input device 108b relative to the manipulator 102a corresponds to a proposed association between the user input device 108a and the manipulator 102a. For example, both the indicator device 124b and the indicator device 126b can provide similar feedback so that the operator 104 can intuitively understand that the proposed association is between the user input device 108b and the manipulator 102b (and, e.g., not between the user input device 108b and the manipulator 102a). In some cases, this feedback is provided as the operator 104 moves the user input device 108b. As a result, the operator 104 is able to easily determine when the user input device 108b has been appropriately moved to satisfy the association condition to associate the user input device 108b and the manipulator 102b (and, e.g., to not satisfy the association condition to associate the user input device 108a and the manipulator 102b). As described with respect to the process illustrated in FIG. 7, in some cases, the operator 104 provides confirmation of the proposed association so that the controller 110 proceeds with associating the manipulator 102b with the user input device 108b. Also, in some implementations, the indicator devices 124b, 126b can indicate, after the association is made, that the user input device 108b is associated with the manipulator 102b. For example, the indicator devices 124a, 126a provide similar or identical feedback for part or the entire duration that the user input device 108b is associated with the manipulator 102b.

Figure 4:
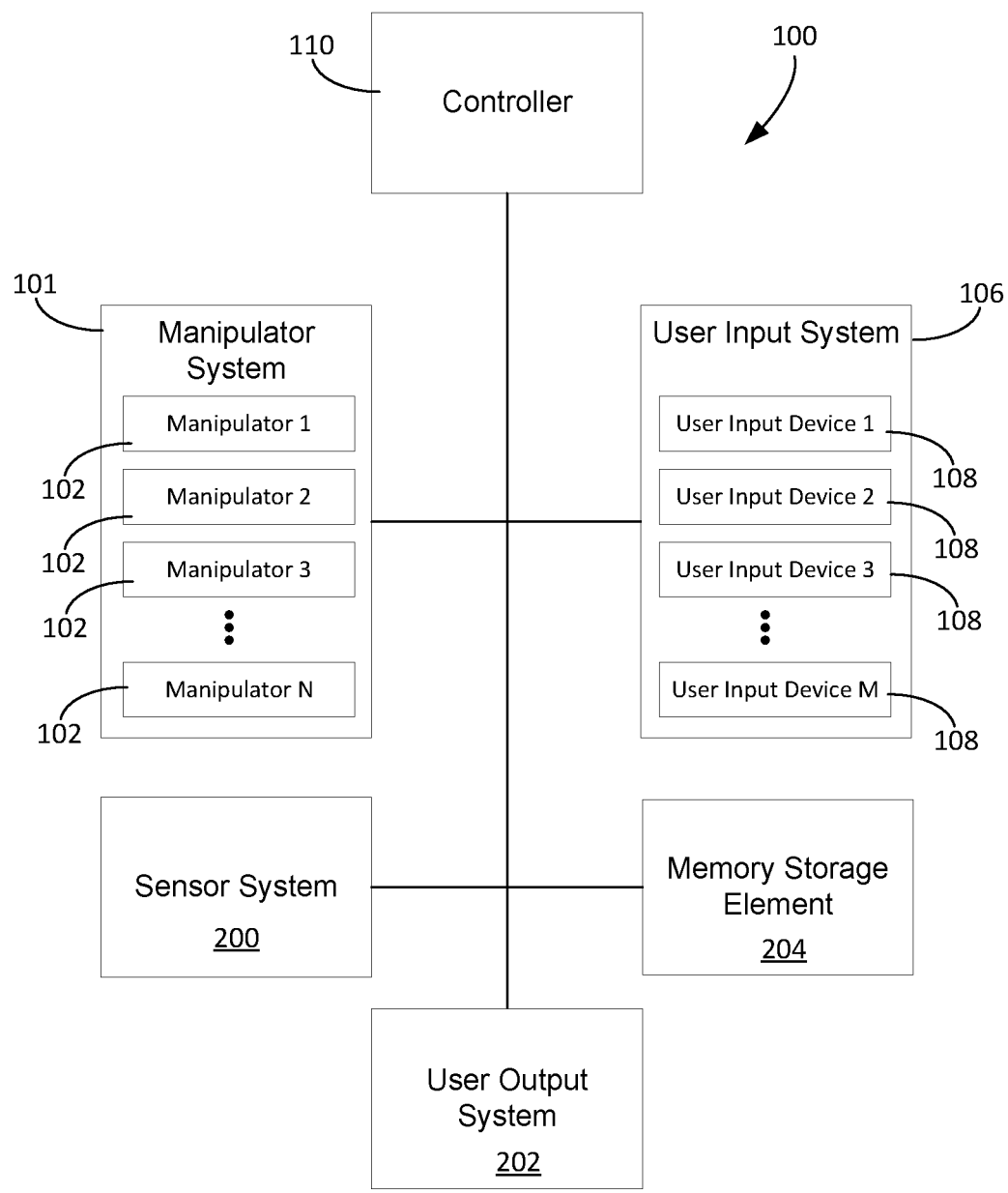
FIG. 4 is a block diagram of a system for performing a manipulator association process.

Referring to FIG. 4 and as described herein, an example of the system 100 for performing an association process includes the manipulator system 101, the controller 110, and the user input system 106. While described with respect to FIGS. 1, 2, 3A, and 3B as including two or four manipulators, in some implementations, as shown in FIG. 4, the manipulator system 101 can include any number of manipulators. For example, the manipulator system 101 includes N manipulators (e.g., Manipulator 1 through Manipulator N, collectively referred to as manipulators 102). Similarly, while described with respect to FIGS. 1, 2, 3A, and 3B as including two user input devices, in some implementations, as shown in FIG. 4, the user input system 106 includes any number user input devices. For example, the user input system 106 includes M user input devices (e.g., User Input Device 1 through User Input Device M, collectively referred to as user input devices 108). Examples of the user input devices 108 include: joysticks, touchscreens, gloves, or handheld remotes.

The system 100 can further include a sensor system 200. The sensor system 200 includes sensors operable to detect movement the user input devices 108. For example, the sensor system 200 includes the sensors 128a, 128b (shown in FIGS. 3A and 3B). The sensors, in particular, can detect movement of the user input devices 108 that satisfy association conditions for associating a particular user input device with a particular manipulator. The sensor system 200 can detect poses, e.g., positions, orientations, or both positions and orientations, of the user input devices 108 and the manipulators 102 in the environment 10. Sensors of the sensor system 200 include, for example, infrared sensors, ultrasonic sensors, image capture devices, accelerometers, position encoders, optical sensors, or other appropriate sensors for detecting motion and poses of the manipulators 102 and the user input devices 108. Further examples of association conditions and sensors for detecting these association conditions are described with respect to the process illustrated in FIG. 7.

The system 100 can further include a user output system 202 and a memory storage element 204. The user output system 202 provides human-perceptible feedback to the operator 104. The user output system 202 includes, for example, the indicator system 122 or the display system 107. In this regard, the feedback provided by the user output system 202 can include feedback provided during an association process or during following mode.

Figure 5:
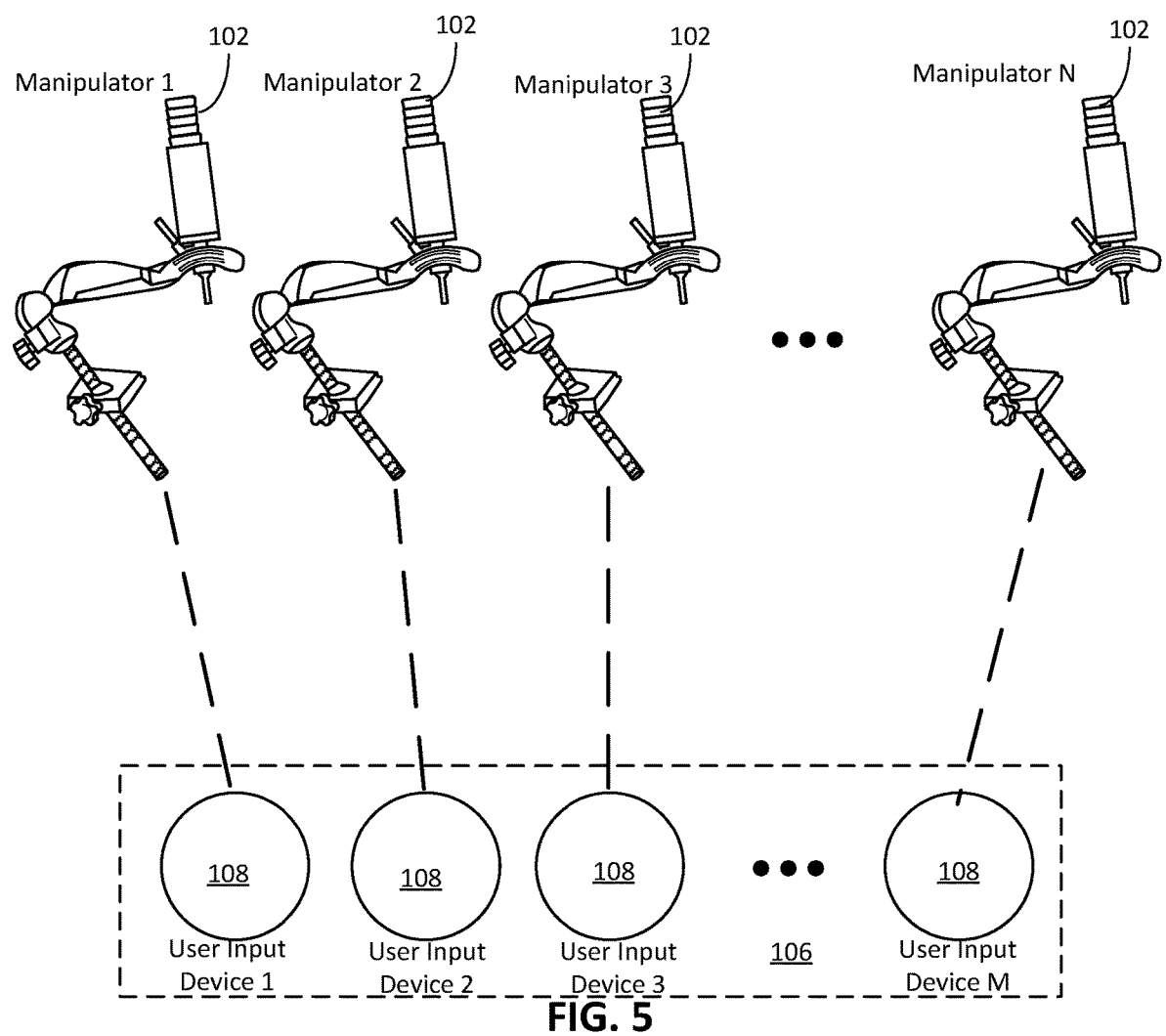
FIG. 5 is a diagram illustrating associations between manipulators and user input devices.

The memory storage element 204 can store data indicative of associations formed between the manipulators 102 and the user input devices 108. The controller 110 can retrieve these stored data to determine whether a user input device or a manipulator is in an associated state or an unassociated state. Referring to FIG. 5, the manipulators 102 and the user input devices 108 are associated so that each user input device 108 is associated with a distinct one of the manipulators 102. As a result, the user input devices 108 can be controlled by the operator 104 so that the associated manipulators can be independently controlled. In some cases, each of the manipulators 102 is associated with a corresponding one of the user input devices 108. As a result, each of the manipulators 102 can be controlled using the user input devices 108.

Example Processes

Figure 6:
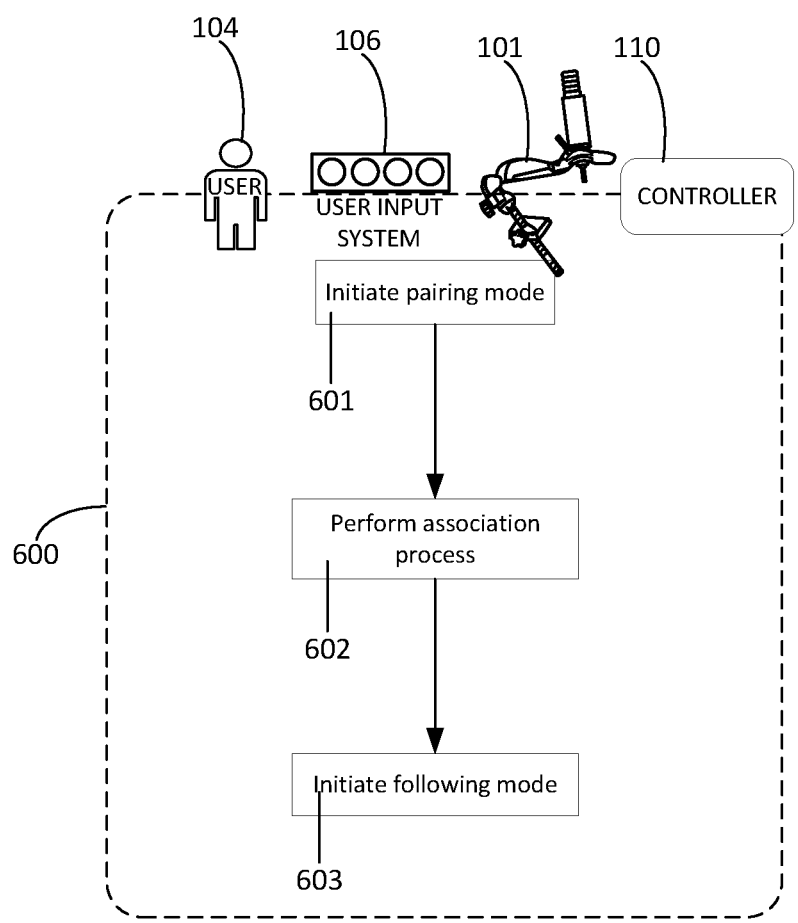
FIG. 6 is a flowchart illustrating a process of operating a user input system to control a manipulator system.

Referring to FIG. 6, a process 600 including an association process and a following process is presented with respect to the system 100 described herein. The process 600 is performed by the operator 104, the user input system 106, the manipulator system 101, the controller 110, or a combination of the foregoing. At operation 601, a pairing mode is initiated. At operation 602, the association process is performed to associate a manipulator with a user input device. Examples of further operations and sub-operations the operations 601 and 602 are described with respect to FIGS. 7, 8A, 8B, and 9.

At operation 603, a following mode is initiated so that, in a following process, the manipulator can be controlled in response to manipulation of the user input device. In the following mode, the manipulator associated with the user input device at operation 602 can be moved in response to manual operation of the user input device by the operator 104. The operator manually manipulates the user input device, which generates a signal or indication received by the controller 110. The controller 110 then generates a corresponding signal to move the manipulator of the manipulator system 101 with which the user input device is associated. In this regard, the user input device and the manipulator form a leader-follower system in which the user input device is a leader device and the manipulator is a follower device, thereby enabling the manipulator to be teleoperated through operation of the user input device. If the system 100 is a surgical system, an instrument supported by the manipulator can be controlled to perform a surgical operation on a patient.

Figure 7:
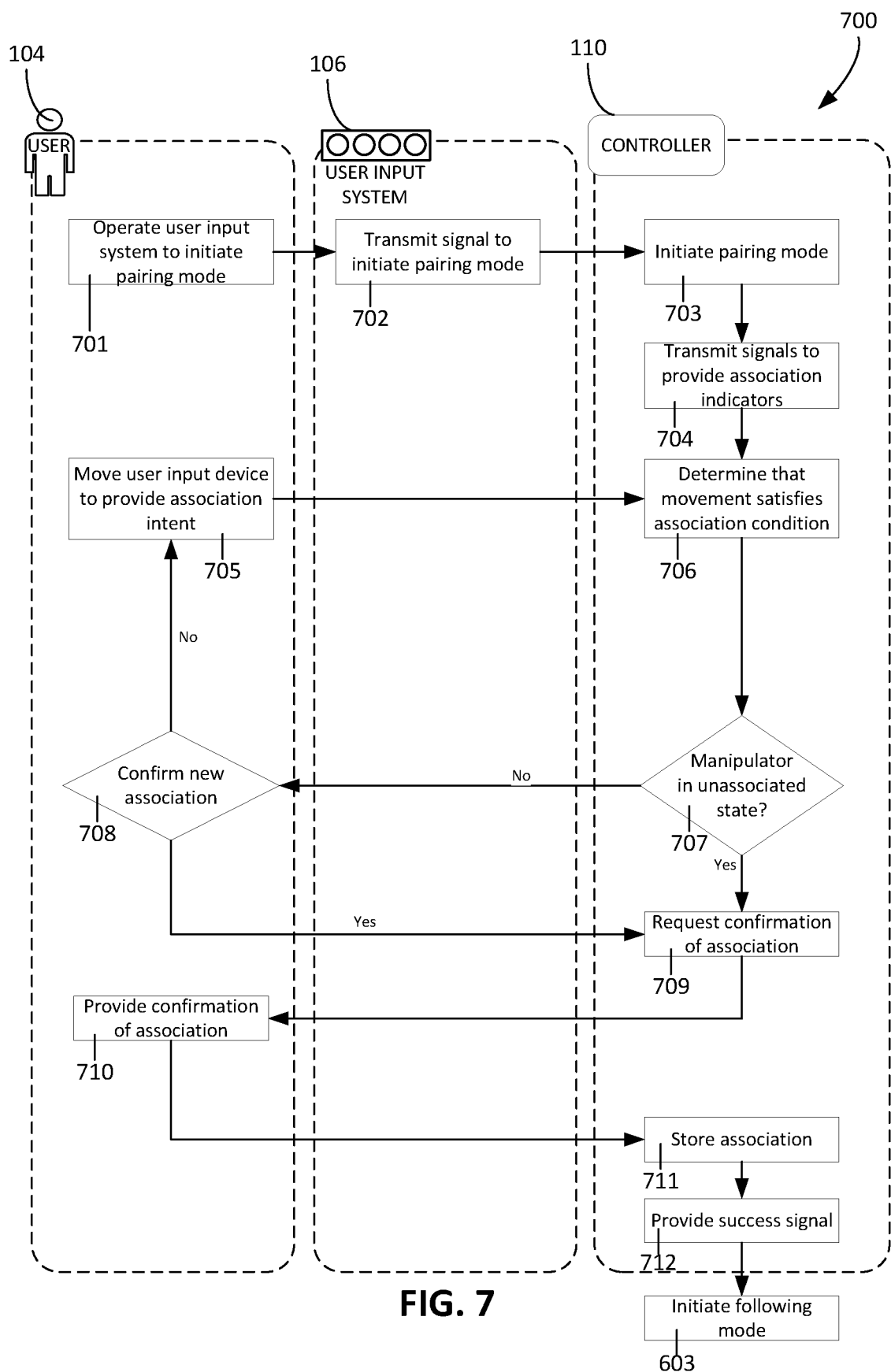
FIG. 7 is a flowchart illustrating a process to associate a user input device with a manipulator.

FIG. 7 illustrates an example of a process 700 to associate a user input device of the user input system 106 with a manipulator of the manipulator system 101. The process 700 is performed, for example, during the operations 601 and 602 described with respect to the process 600.

Operations 701-703 of FIG. 7 illustrate an example process of initiating a pairing mode. At operation 701 of the process 700, the operator 104 operates the user input system 106 to initiate the pairing mode. For example, the user input system 106 includes a user input device dedicated to initialization of the pairing mode. This user input device can be distinct from the user input devices that are associated to manipulators. At operation 702, the user input system 106 transmits a signal to the controller 110 to initiate the pairing mode, e.g., in response to the operator 104 operating the user input system 106 to initiate the pairing mode. At operation 703, the controller 110 initiates the pairing mode, e.g., in response to the signal transmitted at the operation 702.

During the pairing mode, the operator 104 provides an association intent to associate a particular user input device with a particular manipulator. In addition, feedback is provided to the operator 104 so that the operator 104 can be kept informed of states of the manipulators of the manipulator system 101 and the user input devices of the user input system 106. Operations 704-712 illustrate examples of operations that occur during the pairing mode and in which the foregoing can occur.

In some examples, after the pairing mode is initiated at operation 703, at operation 704, the controller 110 transmits signals to provide association indicators to the operator 104. The signals can be transmitted to the user output system 202 (shown in FIG. 4), e.g., the indicator system 122 (shown in FIGS. 3A and 3B) or the display system 107 (shown in FIG. 1). The user output system 202 presents the association indicators to indicate an association state of each of the manipulators of the manipulator system 101 and an association state of each of the user input devices of the user input system 106.

At operation 705, the operator 104 moves a user input device (e.g., one of the user input devices 108 described with respect to FIG. 4) to provide an association intent. The movement of the user input device corresponds to an intent to associate the user input device with a manipulator of the manipulator system 101 (e.g., one of the manipulators 102 described with respect to FIG. 4).

Based on the movement of the user input device, a signal indicative of the movement of the user input device is transmitted to the controller 110. The signal is transmitted by the sensor system 200 (shown in FIG. 4) to the controller 110.

At operation 706, based on the signal indicative of the movement of the user input device, the controller 110 determines whether the movement of the user input device satisfies an association condition. Association conditions can vary between implementations.

In some examples, the association condition includes contact between a particular user input device and a particular manipulator. The sensor system 200 includes a contact sensor, e.g., a capacitive sensor, that detects contact between the user input device and the manipulator intended to be associated with the user input device. The contact sensor can be attached to or positioned on the user input device or the manipulator. In some implementations, the user input device includes a contact sensor, and the manipulator also includes a contact sensor. The association condition is satisfied when the contact sensors detect contact with one another.

In some implementations, the association condition includes proximity between the user input device and the manipulator. For example, the association condition is satisfied when the user input device is move to a region within a predefined distance from the manipulator, e.g., within 5 cm, within 10 cm, within 20 cm, within 30 cm, or within 50 cm. The sensor system 200 includes a proximity sensor that detects when the user input device is moved to within the predefined distance. For example, the proximity sensor can include a sensor to detect the distance between the user input device and the manipulator, e.g., a time-of-flight sensor, an infrared sensor, or an ultrasonic sensor. In some examples, the proximity sensor includes a sensor attached to one of the manipulator or the user input device and a detectable tag on the other of the manipulator or the user input device. The sensor can be a radiofrequency detector, and the tag can be a radiofrequency tag.

In some implementations, the association condition includes a motion of the user input device directed toward a region defined by a location of the manipulator in the workspace. For example, each of the manipulators defines a corresponding volume. The volume defined by a manipulator can be within the workspace of the manipulator or can extend outside of the workspace. In some cases, the volume is defined by physical surface of the manipulator. The motion of the user input device includes a direction, e.g., a direction of a velocity or acceleration of the user input device. The association condition for a manipulator is satisfied when the direction of the motion is directed toward the volume defined by the manipulator, e.g., the ray defined by the direction of the motion intersects with the volume. The sensor can be an accelerometer coupled to the user input device. The accelerometer can detect the direction of the motion of the user input device. In implementations in which multiple user input devices are associated with multiple manipulators in the pairing mode, locations of the multiple manipulators define multiple distinct regions. The operator moves the user input device toward a first region to satisfy the association condition for a first manipulator, and the operator moves the user input device toward a second region to satisfy the association condition for a second manipulator.

Contact between the manipulator and the user input device, proximity between the manipulator and the user input device, and direction of movement of the user input device can be detected in other manners. For example, in some implementations, an image capture device of the sensor system 200 captures imagery of the environment 10 (shown in FIG. 1). Contact, proximity, and direction of movement can be determined using image analysis of the captured imagery. The image capture device can be a stationary camera positioned to capture imagery of the manipulator system 101 and the user input system 106.

In some implementations, the movement of the user input device in the pairing mode corresponds to ambiguous movement that does not satisfy a single association condition for a single manipulator. In some cases, the association conditions for multiple manipulators are satisfied due to a single motion of the user input device. In such cases, the controller 110 does not associate a manipulator with the user input device until an association condition of only one of the manipulators is fulfilled. To guide the operator 104 to resolve the ambiguity of multiple association conditions being fulfilled, the controller 110 can control the user output system 202 to provide feedback to the operator 104 indicative of the ambiguity. For example, indicator devices of the manipulators for which the association conditions are satisfied are activated. Multiple indicator devices of the manipulators being activated can be indicative of ambiguity, and the operator 104 can adjust movement of the user input device or can generate other motions of the user input device to resolve the ambiguity.

In some cases, the movement of the user input device in the pairing mode corresponds to a movement that does not satisfy an association condition for any manipulator. The controller 110 can operate the user output system 202 to provide feedback to the operator 104, e.g., to guide the operator to move the user input device in a manner that fulfills an association condition of one of the manipulators. For example, when a movement of the user input device is detected but does not satisfy an association condition for any manipulator, the indicator device for the user input device can provide a warning indication. In some cases, the indicator device emits a yellow light to provide the warning indicator to the operator 104.

After the controller 110 determines that the movement of the user input device satisfies the association condition for a manipulator, at operation 707, the controller 110 determines an association state of the manipulator. The controller 110 determines whether the manipulator is in an unassociated state. For example, the controller 110 can access the memory storage element 204 (shown in FIG. 4) to determine whether an association for the manipulator has been stored on the memory storage element 204. If the manipulator is not in an unassociated state, e.g., in an associated state, the operator 104 at operation 708 either confirms that a new association is to be provided to the manipulator or indicates that the manipulator should maintain the stored association. If the operator 104 confirms that a new association is to be provided, the controller 110 can remove the stored association for the manipulator.

If it is confirmed at the operation 708 that a new association is to be created for the manipulator or if it is determined at the operation 707 that the manipulator in an unassociated state, the controller 110 at operation 709 requests for confirmation of an association between the user input device and the manipulator. For example, the controller 110 transmits data representing the request for confirmation to the user output system 202. In some implementations, the indicator device on the user input device and the indicator device on the manipulator both provide a feedback pattern indicative of a pending association. If the indicator devices are light indicator devices, the indicator devices can both flash a same color (e.g. green), number, text, graphics, or in a same time sequence, or provide some other visual feedback to indicate that the condition for association between the manipulator and the user input device has been satisfied and confirmation from the operator 104 is requested.

At operation 710, the operator 104 provides the confirmation of the association. In some implementations, the operator 104 can provide this confirmation by performing a specific manipulation of the user input device to confirm the association. The specific manipulation can include a movement of the user input device detectable by the sensor system 200, e.g., shaking the user input device up-and-down or directing a movement of the user input device towards the display system 107. The specific manipulation can include a manipulation of the user input device for controlling motion of the manipulator in a following mode. For example, if the user input device includes a joystick, a button, knob, or other user input element, the operator 104 can operate the user input element to confirm the association.

At operation 711, after receiving confirmation of the association, the controller 110 stores the association, e.g., in the memory storage element 204. The controller 110 then provides a success signal at operation 712. For example, the user output system 202 is operated to provide a human-perceptible signal indicative of the success of the association between the manipulator and the user input element.

While described with respect to associating a single user input device with a single manipulator, in some implementations, the operations 704-712 can be repeated to associate other user input devices of the user input system 106 with other manipulators of the manipulator system 101. The system 100 can remain in the pairing mode until the operator 104 operates the user input system 106 to provide input indicative of initiating the following mode, e.g., initiating operation 603. In the following mode, the user input devices that have been associated with the manipulators can be operated by the operator 104 to control movement of the manipulators.

Figure 8A:
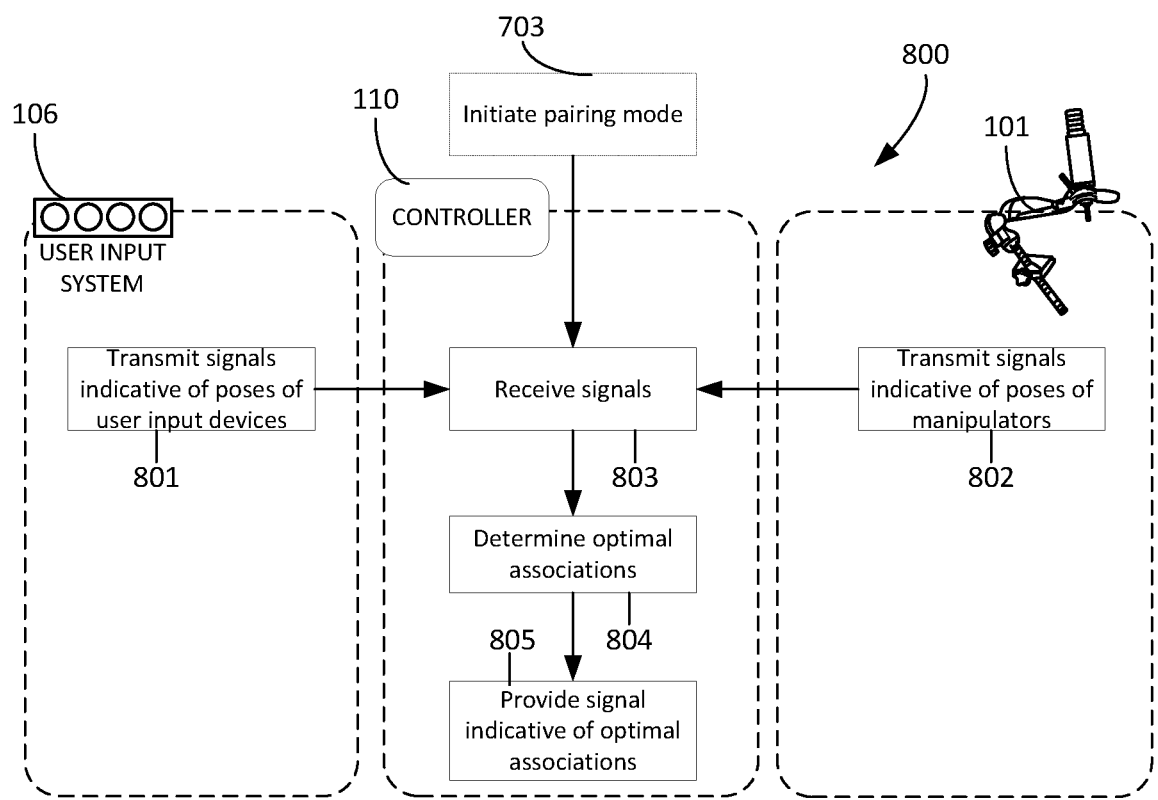
FIG. 8A is a flowchart illustrating a process to optimize associations formed between manipulators and user input devices.

In some implementations, the controller 110 can provide recommendations to optimize the associations formed between the manipulators and the user input devices. Process 800 of FIG. 8A illustrates an example process to provide such a recommendation. The process 800 is initiated after the pairing mode is initiated. Upon initiation, at operation 801, the user input system 106 transmits signals indicative of poses of the user input devices of the user input system 106, e.g., poses of the user input devices in the environment 10 (shown in FIG. 1). At operation 802, the manipulator system 101 transmits signals indicative of poses of the manipulators of the manipulator system 101 to the controller 110. At operation 803, the controller 110 receives these signals from the user input system 106 and the manipulator system 101. In some implementations, the sensor system 200 detects the poses of the user input devices, the manipulators, or both and transmits these signals to the controller 110. In addition, the controller 110 further receives a signal indicative of the position and the orientation of the image capture device, e.g., on the instrument supported on the manipulator 102c.

The controller 110 receives the signals and uses kinematic modeling to determine the positions and orientations of the manipulators 102a, 102b, the positions and orientations of the instruments 116a, 116b, and the position and orientation of the image capture device. In some cases, one or more signals are generated by sensors of the manipulators (e.g., the manipulators 102a, 102b, and the manipulator to which the image capture device is mounted) or sensors of the instruments (e.g., the instruments 116a, 116b, and the image capture device). The sensors of the manipulators include, for example, accelerometers, gyroscopes, encoders, or other sensors associated with joints of the manipulators 102a, 102b. The sensors of the instruments include, for example, shape sensors through shafts of the instruments. Alternatively, the positions and orientations of the manipulators and/or the positions and orientations of the instruments are determined based on one or more signals from optical sensors (e.g., image capture devices). The manipulators or the instruments are equipped with optical fiducials detectable by the optical sensors.

Figure 8B:
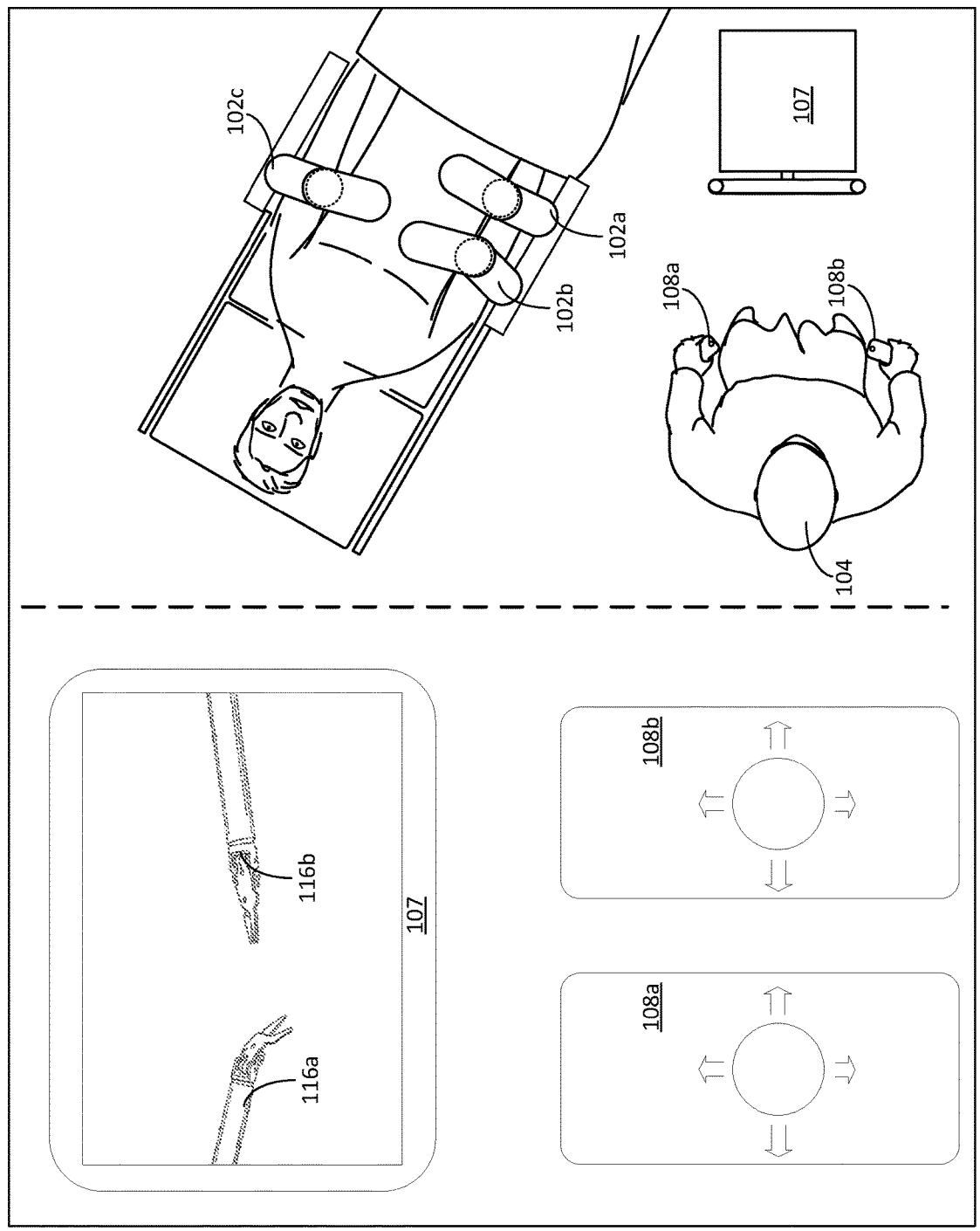
FIG. 8B illustrates, on a left portion of FIG. 8B, a user input system and a display showing instruments and, on a right portion of FIG. 8B, a top view of manipulators supporting the instruments.

At operation 804, based on the received signals, the controller 110 determines usable or optimal associations between the manipulators of the manipulator system 101 and the user input devices of the user input system 106. FIG. 8B illustrates an example in which the manipulators 102a, 102b (shown on the right portion of FIG. 8B) support the instruments 116a, 116b, respectively (shown on the left portion of FIG. 8B). The display system 107 presents imagery captured by an instrument (not shown) with an image capture device supported by the manipulator 102c.

FIG. 8B includes a right portion diagrammatically depicting relative positions of the display system 107 and the user input devices 108, and a left portion showing a top view of the system 100. As shown in FIG. 8B, the instrument 116a appears on a left portion of imagery presented on the display system 107, while the instrument 116b appears on a right portion of the imagery. To provide the operator 104 with intuitive control of the instruments 116a, 116b as the instruments 116a, 116b appear on the display system 107, the controller 110 provides a recommendation to associate the user input device 108a (in the left hand of the operator 104) with the instrument 116a on the left portion of the imagery. Furthermore, the controller 110 provides a recommendation to associate the user input device 108b (in the right hand of the operator 104) with the instrument 116b on the right portion of the imagery. The controller 110 can determine the relative positions and orientations of the user input devices 108a, 108b and the manipulators 102a, 102b based on the signals indicative of the poses of these devices.

Alternatively, in some implementations, the controller 110 determines the positions and orientations of the user input devices 108a, 108b relative to the instruments 116a, 116b supported by the manipulators 102a, 102b. The controller 110 further receives a signal indicative of the position and the orientation of the image capture device, e.g., on the instrument supported on the manipulator 102c. The controller 110 can determine relative poses of the instruments 116a, 116b as they would appear to the operator 104 on the display system 107. The controller 110 can determine a recommendation for the associations between the user input devices 108a, 108b and the manipulators 102a, 102b based on these relative poses. In various implementations, the recommendation may include recommended associations for a subset or all of the user input devices (e.g. 108a, 108b) and a subset or all of the manipulators (102a, 102b). Also, in various implementations, the recommendations may indicate degrees of recommendation for a particular association, such as: a more recommended association between a user input device and a manipulator (e.g. between the user input device 108a and the manipulator holding the instrument 116a), a less recommended association between a user input device and a manipulator (e.g. between the user input device 108a and a manipulator holding an instrument not shown in the imagery), or a not recommended association between a user input device and a manipulator (e.g. the user input device 108a and a manipulator holding the instrument 116b).

In some implementations, the controller 110 does not receive positions and orientations of the user input devices 108a, 108b for determining the recommendations. The user input devices 108a, 108b can be configured such that the user input devices 108a, 108b have fixed positions and orientations relative to one another. In this regard, the controller 110 can provide a recommendation based on the positions and orientations of the manipulators 102a, 102b relative to one another or based on the positions and orientations of the instruments 116a, 116b relative to one another.

After the controller 110 determines the optimal associations, the controller 110 at operation 805 provides a signal to indicate the optimal associations to the operator 104. For example, the controller 110 controls the user output system 202 to provide an appropriate signal to guide the operator 104 to form the optimal associations between the manipulators 102a, 102b and the user input devices 108a, 108b. If the manipulators 102a, 102b and the user input devices 108a, 108b include light indicator devices, the light indicator devices for corresponding devices that the controller 110 recommends associating can emit like optical signals, e.g., optical signals having a similar color. These optical signals can be distinct from the optical signals emitted by the light indicator devices of other corresponding devices that the controller 110 recommends associating. These optical signals can thus provide guidance to the operator 104 to intuitively form the optimal associations, e.g., using the process 700. Alternatively, in some implementations, rather than the process 700 being execute to form the optimal associations, the controller 110 automatically forms the associations between the manipulators 102a, 102b and the user input devices 108a, 108b based on the determined optimal associations.

Figure 9:
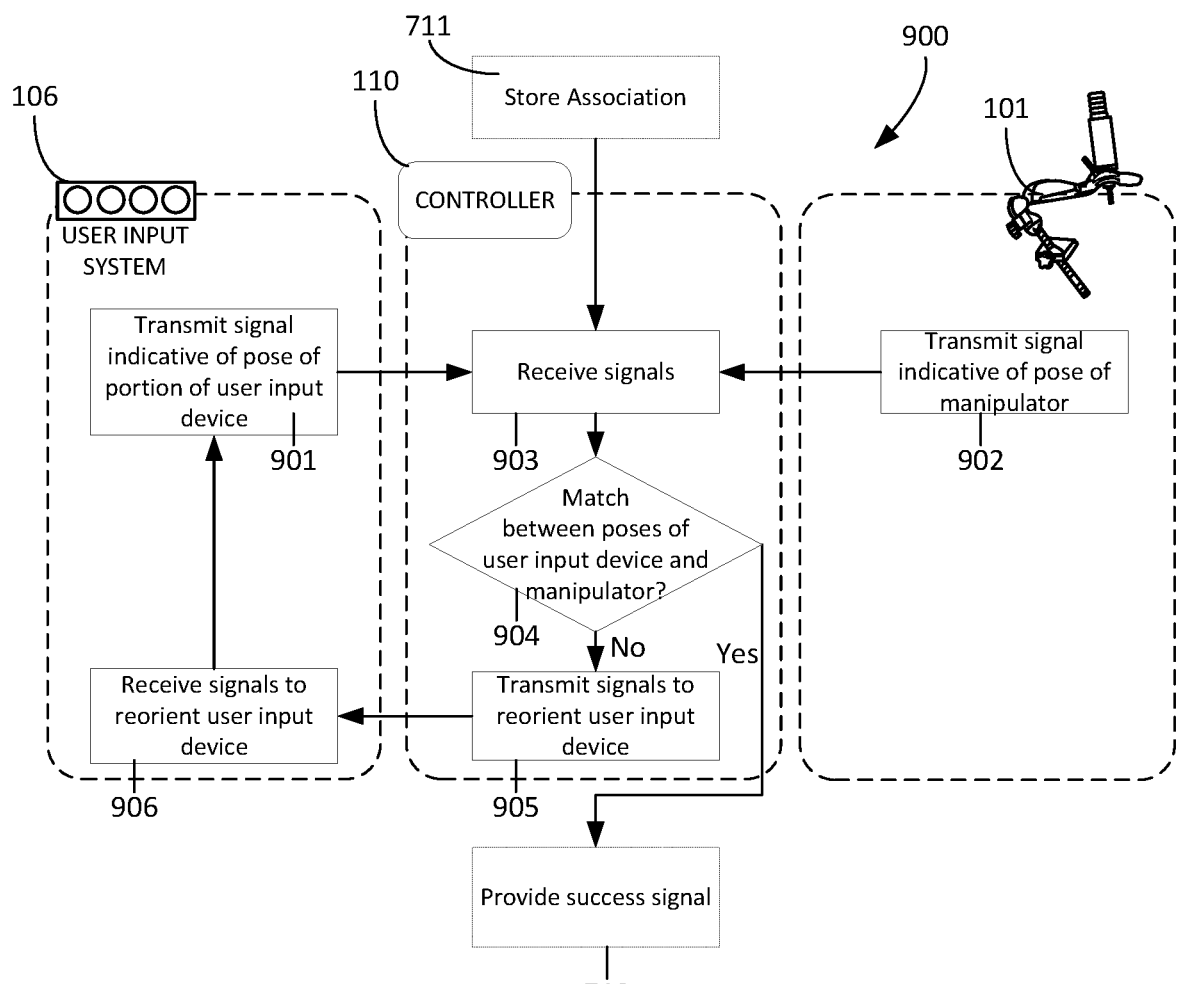
FIG. 9 is a flowchart illustrating a process to reorient user input devices.

In some implementations, prior to initiating the following mode and after the associations between user input devices and manipulators are formed, for each user input device, the controller 110 can determine a pose of a portion of the user input device relative to a pose of the manipulator. For example, the portion of the user input device is manually operable by the operator 104 to control movement of the manipulator during the following mode. To ensure that the operator 104 can control the manipulator 102 through its full range of motion using the user input device, the portion of the user input device can be reoriented or repositioned. Process 900 of FIG. 9 is performed to achieve this reorienting or repositioning of a portion of a user input device.

At operation 901, the user input system 106 transmits a signal indicative of a pose of a portion of a user input device of the user input system 106. For example, the signal is indicative of the position and orientation of the portion of the user input device relative to the full range of motion of the portion. A position sensor coupled to the portion of the user input device can generate the signal. At operation 902, the manipulator system 101 transmits a signal indicative of a pose of a manipulator of the manipulator system 101. Position sensors of the manipulator, e.g., encoders, accelerometers, etc., can generate and transmit the signal. At operation 903, the controller 110 receives these signals from the user input system 106 and the manipulator system 101.

Based on these signals, at operation 904, the controller 110 determines whether a pose of the user input device relative to a full range of motion of the portion matches with a pose of the manipulator relative to a full range of motion of the manipulator. For example, the user input device can have a degree of freedom of motion for controlling yaw motion of the distal end of the manipulator. The controller 110 determines whether the position of the user input device within the full range of motion for this degree of freedom of motion matches with the position of the distal end of the manipulator within the full range of motion for its yaw degree of freedom. The controller 110 similarly compares the position of the portion of the user input device for each of its other degrees of freedom to the position of the manipulator for its other degrees of freedom.

If the poses of the portion of the user input device and the manipulator do not match, the controller 110 at operation 905 transmits signals to reorient the portion of the user input device. At operation 906, the user input system 106 receives the signals. In some cases, the signals cause automatic motion of the portion of the user input device. For example, the signals drive one or more actuators to move the portion of the user input device. Alternatively, the user input system 106 provides feedback to the operator 104 to reorient or reposition the portion of the user input device. The user input system 106 then at operation 901 transmits another signal indicative of the pose of the portion of the user input device, and the controller 110 determines again whether there is match between the poses of the portion of the user input device and the manipulator.

When the controller 110 determines a match at operation 904, the following mode can be initiated. For example, the success signal can be provided at the operation 712 of the process 700, and the following mode can then be initiated.

Further Implementations

A number of implementations have been described. Nevertheless, it will be understood that various modifications may be made.

Figure 10:
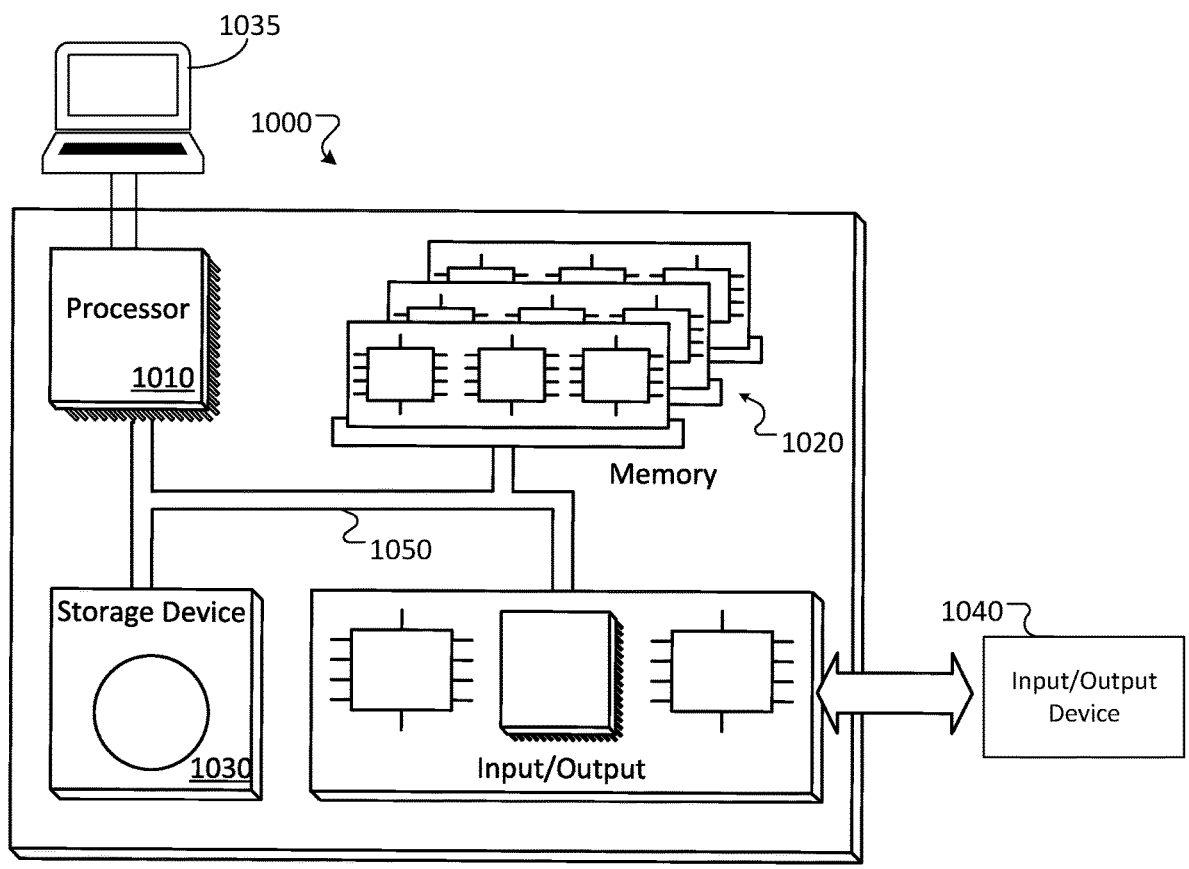
FIG. 10 is a schematic diagram of a computer system.

For example, controllers and any associated components described herein can be part of a computing system that facilitates control of the systems according to processes and methods described herein. FIG. 10 is a schematic diagram of an example of a computer system 1000 that can be used to implement a controller, e.g., the controller 110 or other controller of the system 100, described in association with any of the computer-implemented methods described herein, e.g., methods including one or more of the processes and operations described with respect to FIGS. 6-9. The system 1000 includes components such as a processor 1010, a memory 1020, a storage device 1030, and an input/output device 1040. The components 1010, 1020, 1030, and 1040 are interconnected using a system bus 1050. The processor 1010 is capable of processing instructions for execution within the system 1000. In some examples, the processor 1010 is a single-threaded processor, while in some cases, the processor 1010 is a multi-threaded processor. The processor 1010 is capable of processing instructions stored in the memory 1020 or on the storage device 1030 to display graphical information for a user interface on the input/output device 1040.

Memory storage for the system 1000 can include the memory 1020 as well as the storage device 1030. The memory 1020 stores information within the system 1000. The information can be used by the processor 1010 in performing processes and methods described herein. In some examples, the memory 1020 is a computer-readable storage medium. The memory 1020 can include volatile memory and/or non-volatile memory. The storage device 1030 is capable of providing mass storage for the system 1000. In general, the storage device 1030 can include any non-transitory tangible media configured to store computer readable instructions. Optionally, the storage device 1030 is a computer-readable medium. Alternatively, the storage device 1030 may be a floppy disk device, a hard disk device, an optical disk device, or a tape device.

In some cases, the processor 1010 is in communication with a remote computing system 1035. The remote computing system 1035 includes, for example, a remote server, a cloud computing device, or other computing device remote from the processor 1010 and its systems. The remote computing system 1035 includes computing resources remote from the environment of the processor 1010, e.g., remote from the surgical environment. In some cases, the remote computing system 1035 includes one or more servers that establish wireless links with the processor 1010. The remote computing system 1035 includes, for example, a portion of a network-accessible computing platform implemented as a computing infrastructure of processors, storage, software, data access, and so forth accessible by the processor 1010.

The system 1000 includes the input/output device 1040. The input/output device 1040 provides input/output operations for the system 1000. In some examples, the input/output device 1040 includes a keyboard, a computer mouse, a pointing device, a voice-activated device, a microphone, a touchscreen, etc. In some cases, the input/output device 1040 includes a display unit for displaying graphical user interfaces.

The features of the methods and systems described in this application can be implemented in digital electronic circuitry, or in computer hardware, firmware, or in combinations of them. The features can be implemented in a computer program product tangibly stored in an information carrier. The information carrier can be, for example, a machine-readable storage device, for execution by a programmable processor. Operations, e.g., of the processes 600, 700, 800, and 900, can be performed by a programmable processor executing a program of instructions to perform the functions described herein by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages. The computer program can be deployed in any form, including as a stand-alone program or as a module, component, subroutine, or other unit suitable for use in a computing environment. The computer program implements, for example, a fast genetic algorithm (FGA).

Generally, a computer will also include, or be operatively coupled to communicate with, one or more mass storage devices for storing data files. Such devices can include magnetic disks, such as internal hard disks and removable disks, magneto-optical disks, and optical disks. Storage devices suitable for storing the computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

The processor 1010 carries out instructions related to a computer program. The processor 1010 can include hardware such as logic gates, adders, multipliers and counters. The processor 1010 can further include a separate arithmetic logic unit (ALU) that performs arithmetic and logical operations.

Figure 11:
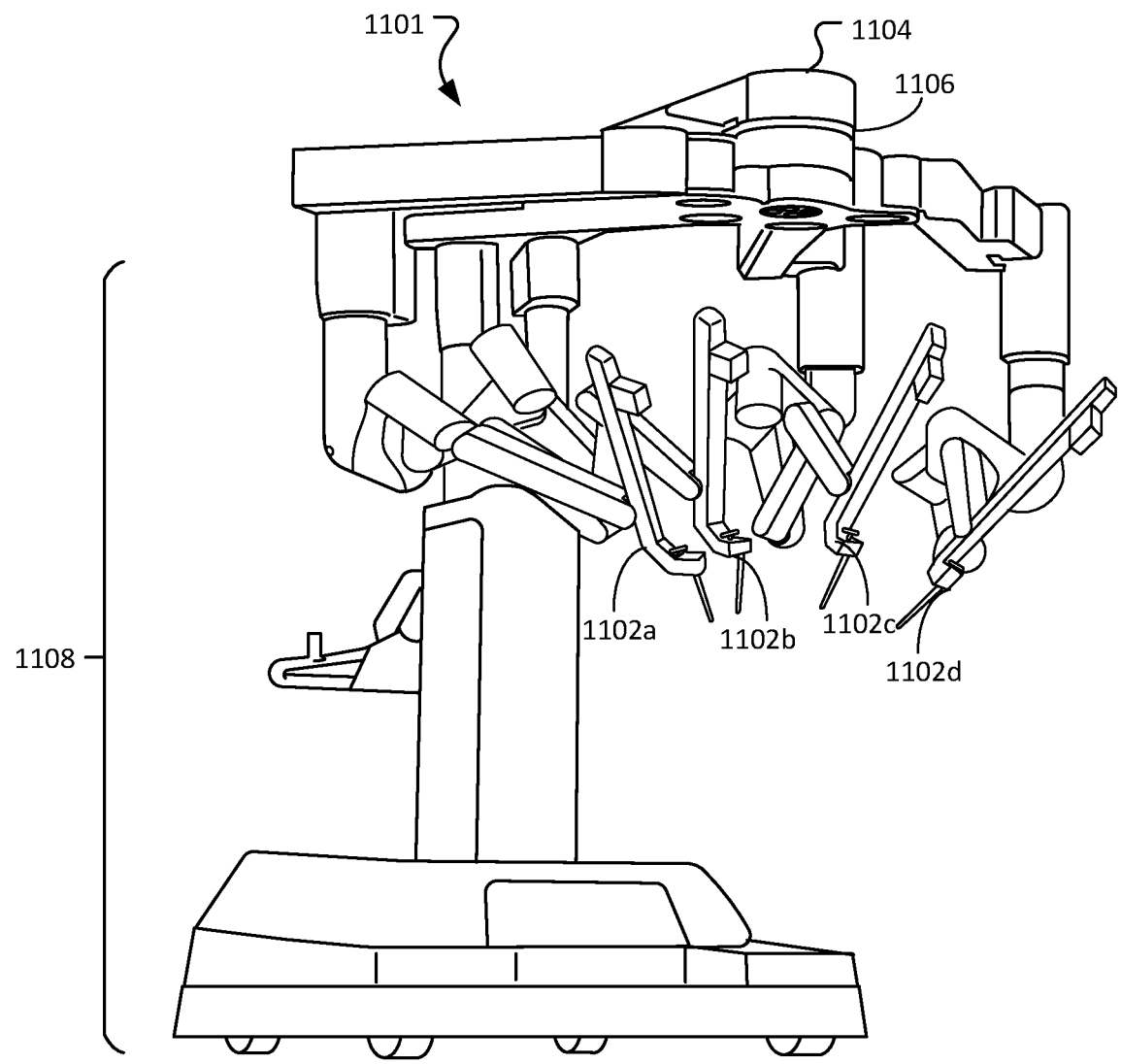
FIG. 11 is a front perspective view of a manipulator system.

While the manipulators 102 are described and shown as being distinct manipulators separately mounted with mounting locations movable relative to each other, e.g., to an operating table, the association processes described herein are also applicable to manipulators that are mounted to a shared base. For example, referring to FIG. 11, a manipulator system 1101 includes manipulators 1102a, 1102b, 1102c, 1102d (collectively referred to as manipulators 1102), each of which is mounted to a common base 1104. A joint 1106 can be driven to reorient all of the manipulators 1102. The base 1104 can be mounted to a movable cart portion 1108. The movable cart portion 1108 is, for example, supported above a floor surface by wheels. In this regard, the manipulator system 1101 is easily movable about an environment.

Figure 12:
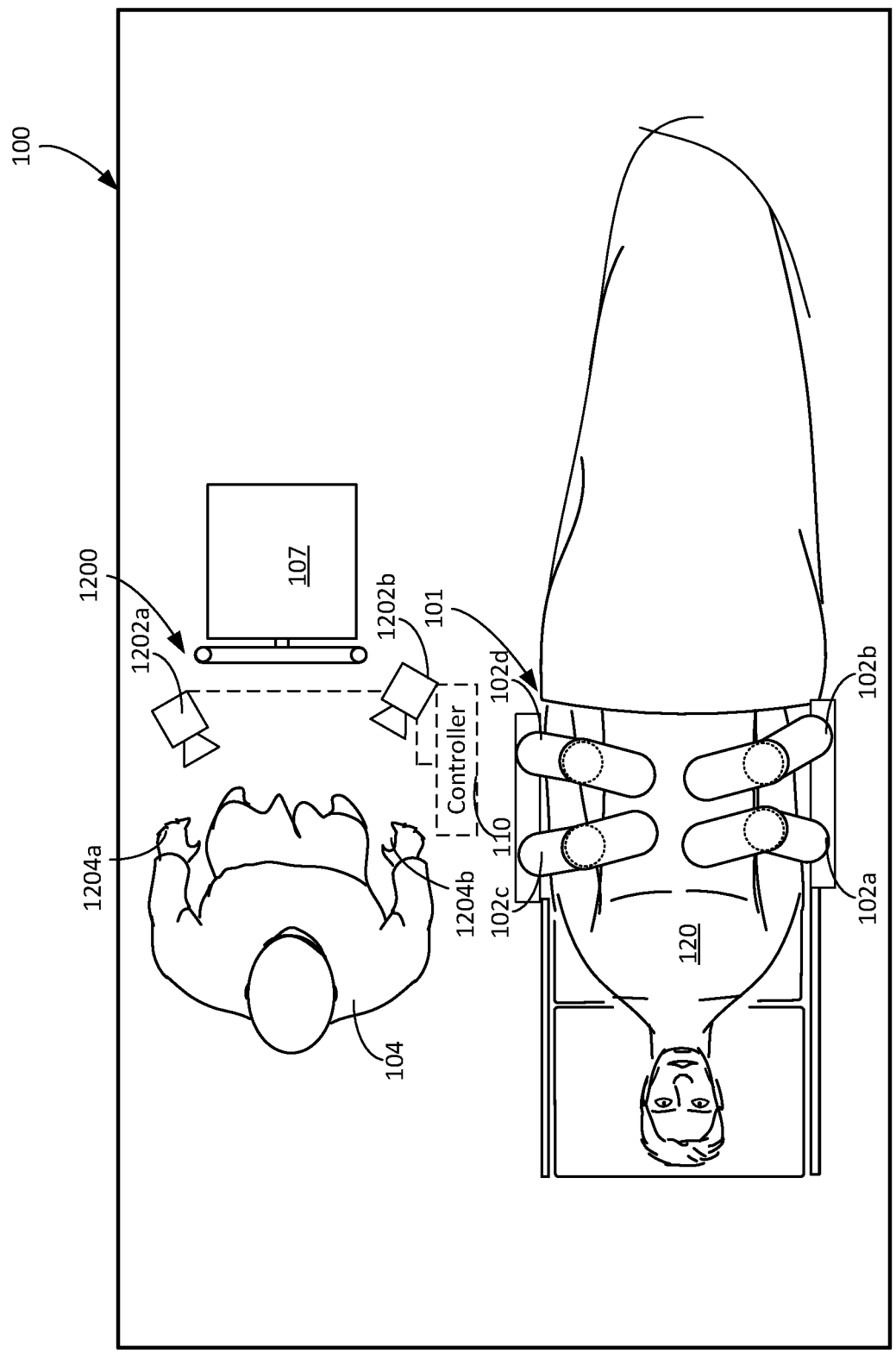
FIG. 12 is a top view of a system including an optical motion detection system.

While the processes have been described as being used for association of the user input devices 108 with the manipulators 102, in some implementations, the system 100 includes one or more sensors that detect motion and form an association based on the detected motion. For example, the processes described herein are used for association of hands of the operator 104 with are described as being handheld. Referring to FIG. 12, in some implementations, the system 100 includes an optical motion detection system 1200 including optical sensors 1202a, 1202b. The optical sensors 1202a, 1202b can provide a stereoscopic imagery of the operator 104 and can be used to detect motion of the operator 104, in particular, motion of hands 1204a, 1204b of the operator 104. Movements of the hands 1204a, 1204b can be used to control movement of the manipulators 102. For example, the hands 1204a, 1204b are moved in a pattern or sequence in accordance with predefined gestures for controlling the system 100. The predefined gestures can include a gesture for initiating a pairing mode, a gesture for proposing an association between a hand and a manipulator, a gesture for initiating a following mode, or other appropriate gesture to control the system 100. In some implementations, the hands 1204a, 1204b are equipped with gloves detectable by the optical motion detection system 1200.

In addition, in the pairing processes described herein, rather than moving the user input devices 108 to form associations with the manipulators 102, the operator 104 moves hands 1204a, 1204b to form associations between the manipulators 102 and the hands 1204a, 1204b. The optical motion detection system 1200 detects the movements of the hands 1204a, 1204b, and the controller 110 determines the association to be formed based on the movements of the hands 1204a, 1204b. The hands 1204a, 1204b can be moved in manners similar to the movements described for the user input devices for satisfying association conditions. When the hands 1204a, 1204b are moved in a manner to satisfy the association conditions, the controller 110 forms the associations between the hands 1204a, 1204b and the corresponding manipulators. For example, at operation 705, rather than moving a user input device, the operator 104 moves a hand 1204a or a hand 1204b. The hands 1204a, 1204b can then be used in the following mode to control motion of the manipulators.

In some implementations, the one or more sensors for detecting motion include any three-dimensional position sensor, such as a magnetic field sensor or an optical sensor. The one or more sensors can include a motion-gravity sensor such as an inertial motion unit (IMU), a gyroscope, a magnetic field compass, or other appropriate sensor for detecting acceleration.

While the indicator system 122 is described as including the indicator devices 124a, 124b, 126a, 126b, the indicator system 122 varies in other implementations. In some cases, the indicator system 122 includes the display system 107. The display system 107 presents visual feedback to the operator 104 during the association process. Alternatively or additionally, the indicator system 122 includes an augmented reality interface. For example, the operator 104 can be equipped with a head-mounted augmented reality system that presents virtual indicators proximate the manipulators 102 and the user input devices 108 to provide feedback during the association process. The augmented reality system can present an indicator proximate a particular manipulator to indicate an association state of the manipulator, e.g., whether the manipulator is in an unassociated state or an associated state. Such a virtual indicator may present feedback similar to any discussed herein with relation to actual, physical indicators. Also, such a virtual indicator may present feedback particular to augmented reality systems.

The pairing mode can be initiated in response to a particular event. For example, operations 701-703 illustrate a particular example of initiating the pairing mode in response to operation of the user input system 106. In some implementations, the user input device of the user input system 106 that is operated to initiate the pairing mode corresponds to a user input device operable to initiate a clutching mode in which the manipulators can be manually repositioned. In the clutching mode, brake systems of the manipulators are disabled or joints of the manipulators are released so that the manipulators can be manually repositioned by the operator. In some examples, the pairing mode is also initiated when the clutching mode is initiated.

In some implementations, the pairing mode can be initiated in response to events that are not associated with operation of user input devices. For example, the controller 110 can be configured to initiate the pairing mode when the system 100 is initialized. In some cases, the system 100 includes an audio input system that detects voice commands issued by the operator 104. The operator 104 can utter a voice command, and the controller 110 accordingly initiates the pairing mode. Alternatively or additionally, the pairing mode can be initiated when a new operator accesses and operates the user input system 106.

In some implementations, the system 100 includes a sensor, e.g., an image capture system or an optical detection system, to detect whether the operator 104 is positioned to view the display system 107. The pairing mode can be initiated in response to the sensor detecting that the operator 104 is looking away from the display system 107. For example, the sensor can detect that the operator 104 is turned away from the display system 107, e.g., toward the workspace where the manipulators 102 are located. By turning away from the display system 107 toward the workspace, the operator 104 can convey intent to associate a user input device with a manipulator. Accordingly, the controller 110 initiates the pairing mode in response to the detection of the operator 104 turning away from the display system 107. In some cases, the controller 110 initiates the pairing mode in this manner after detection that the operator 104 has turned away from display system 107 for a predefined amount of time, e.g., at least 5 seconds, at least 15 seconds, at least 30 seconds, at least 1 minute.

As described herein, a manipulator is associated with the user input device so that the manipulator is movable in response to certain operations of the user input device. Thus, in some implementations, the associated user input device can be used for controlling movement of the manipulator. Further, in some implementations, the associated user input device is operable to control other functions of the manipulator or an instrument mounted to the manipulator instead of, or in addition to, controlling movement of the manipulator. In this regard, at operation 603, when the following mode is initiated, the manipulator is not necessarily moved in response to operation of the associated user input device but, rather, receives a signal to perform a particular function or cause the instrument to perform a particular function. For example, in some implementations where the instrument is an image capture device, the associated user input device is operable to control an image capture function of the image capture device, such as a zoom setting, a lighting setting, a shutter speed setting, or other image capture setting. As another example, in some implementations where the instrument is a suction or irrigation device, the associated user input device is operable to control the application of suction or irrigation. In some implementations where the instrument is an image capture device, the associated user input device is operable to control the image capture device to capture imagery. In some implementations where the instrument is a cauterizing device or other energy application device, the associated user input device is operable to control the energy application device to apply energy to tissue.

In some implementations, in the pairing mode, multiple manipulators are associated with a single portion of the user input system 106. For example, two or more manipulators can be associated with a single one of the user input devices 108. When a single user input device is associated with multiple manipulators, the user input device is operable to generate movement of each of the manipulators. For example, in some implementations, if the operator 104 wishes to shift the combined workspace of multiple manipulators or their associated instruments to a different workspace, the operator 104 can operate the user input device to shift each of the manipulators to a vicinity of this different workspace. In some implementations, rather than moving each of the manipulators one-by-one to reach the different workspace, the operator 104 can associate all of the manipulators to be moved, with a single user input device and operate the single user input device to move the plurality of manipulators, as a group, to the vicinity of the different workspace.

As another example, in some implementations, multiple manipulators can be associated with a single user input device of the user input devices 108, and the single user input device controls only one of the manipulators at a time. In some implementations, an operator selects which one of the manipulators is to be controlled by operating the single user input device via an appropriate method, such as depression of a button, turning of a dial, clicking of a pedal, voice commands, etc. In some implementations, the operator operates a button or pedal is used to cycle through manipulators of the manipulators until the one to be controlled becomes active.

Alternatively or additionally, two or more user input devices can be associated with a single manipulator. For example, in some implementations, one of the user input devices associated with the manipulator is operable to move the manipulator, while the other of the user input devices associated with the manipulator is operable to control a non-movement function of the manipulator or a function of an instrument mounted to the manipulator. In some implementations, the two or more associated user input devices each is operable to control a different degree of freedom or a different set of degrees of freedom of the manipulator. For example, in some implementations, one of the user input devices is manually operable to control a pitch, a yaw, and a roll motion of the manipulator, while the other of the user input devices is manually operable to control movement of the instrument relative to the manipulator along the insertion axis or to control actuation of an end effector of the instrument. As yet another example, in some implementations, a plurality of user input devices are used to enable a multi-handed input. For example, positions, separation distances, direction of motion, speed of motion of the user input devices, relative to each other or a reference, can be used to control the manipulator or an instrument supported by the manipulator.

As a specific example, in an implementation, two user input devices are associated with a single manipulator holding an imaging system such as a camera. An operator holding a user input devices in each hand can control the imaging system with two-handed combination input that simulates manipulation of the work piece relative to the imaging system. For example, in a camera implementation, combined motion of both input devices away from the operator moves the camera away or causes the camera to zoom out, as if the work piece has been pushed away. As another example, in a camera implementation, combined motion of both input devices around a common center rotates the camera field of view, as if the work piece had been rotated. As a further example, in a camera implementation, an increase in the separation distance between the user input devices causes the camera to zoom out, and a decrease in the separation distance between the user input devices causes the camera to zoom in.

In some implementations, the controller 110 is configured to disassociate one or more user input device 108 from one or more manipulators 102 in response to user input or a system event. As an example, the controller 110 may be configured to disassociate an associated pair of manipulator and user input device in response to receiving a signal indicative of a user request to disassociate the first manipulator and the user input device. As another example, the controller may be configured to disassociate all manipulators associated with a user input device, or all user input devices associated with a manipulator, in response to receiving a signal indicative of a user request to disassociate such user input device or such manipulator. the user input system 106 includes disassociating user input devices for initiating disassociation of the user input devices 108 from the manipulators 102. For example, each user input device 108 may comprise disassociating controls or features. As another example, for each of the user input devices 108, a corresponding one of the disassociating user input devices can be operated to disassociate a user input device 108 from a manipulator. In some cases, operation of a disassociating user input device can also initiate the pairing mode.

Accordingly, other implementations are within the scope of the claims.

What is claimed is:

1. A computer-assisted medical system comprising:
a plurality of manipulators;

a user input system operable to generate signals to control the plurality of manipulators, a portion of the user input system being movable relative to the plurality of manipulators; and a controller configured to execute instructions to perform operations comprising:

initiating a pairing mode, in the pairing mode, associating a first manipulator of the plurality of manipulators with the portion of the user input system based on a first signal generated by the user input system and indicative of movement of the portion of the user input system relative to the first manipulator, initiating a following mode, and, in the following mode, controlling motion of the first manipulator in accordance with a second signal generated by the user input system in response to operation of the portion of the user input system by a user, the second indication being distinct from the first indication.

2. The computer-assisted medical system of claim 1, wherein associating the first manipulator with the portion of the user input system based on the movement of the portion of the user input system relative to the first manipulator comprises:

providing feedback indicative of a proposed association between the portion of the user input system and the first manipulator in response to the movement of the portion of the user input system relative to the first manipulator, and then associating the first manipulator with the portion of the user input system in response to receiving a signal indicative of a user confirmation of the proposed association.

3. The computer-assisted medical system of claim 2, further comprising:

an indicator system to generate a human-perceptible indication of an association state of the first manipulator, wherein the indicator system comprises a plurality of indicator devices, a first indicator device being attached to the first manipulator, and a second indicator device being attached to a second manipulator of the plurality of manipulators.

4. The computer-assisted medical system of claim 1, further comprising:

a sensor system configured to indicate, to the controller, a relative movement between the portion of the user input system and the first manipulator, wherein associating the first manipulator of the plurality of manipulators with the portion of the user input system comprises:

associating the first manipulator with the portion of the user input system in response to the relative movement between the portion of the user input system and the first manipulator satisfying an association condition.

5. The computer-assisted medical system of claim 4, wherein the association condition comprises movement of the portion of the user input system to a region within a predefined distance from the first manipulator.

6. The computer-assisted medical system of claim 4, wherein:

the sensor system comprises a contact sensor on the portion of the user input system or on the first manipulator, the contact sensor being configured to indicate contact between the portion of the user input system and the first manipulator, and the association condition comprises contact between the portion of the user input system and the first manipulator.

7. The computer-assisted medical system of claim 4, wherein the association condition comprises motion of the portion of the user input system being directed toward a first region defined by a location of the first manipulator.

8. The computer-assisted medical system of claim 7, wherein the first region is distinct from a second region defined by a location of a second manipulator of the plurality of manipulators; and wherein the operations further comprise:

in the pairing mode, associating the second manipulator with the portion of the user input system based on motion of the portion of the user input system being directed toward the second region.

9. The computer-assisted medical system of claim 1, wherein the operations further comprise:

initiating the following mode after an orientation of the portion of the user input system is aligned with an orientation of the first manipulator.

10. The computer-assisted medical system of claim 1, wherein associating the first manipulator with the portion of the user input system comprises associating the first manipulator with the portion of the user input system only if the portion of the user input system is in an unassociated state and another of the plurality of manipulators is not associated with the portion of the user input system.

11. The computer-assisted medical system of claim 1, wherein:

the user input system comprises a plurality of user input devices, a first user input device of the plurality of user input devices being operable to generate the first signal, and the operations further comprise:

guiding association of the first manipulator with the portion of the user input system based on positions or orientations of the plurality of manipulators relative to the plurality of user input devices.

12. The computer-assisted medical system of claim 1, further comprising a display device to present imagery of a plurality of instruments supported by the plurality of manipulators, wherein the operations further comprise:

initiating the pairing mode only if the user is positioned to view the imagery presented by the display device.

13. The computer-assisted medical system of claim 1, wherein the operations further comprise:

in the pairing mode, completing association of the first manipulator with the portion of the user input system in response to a confirmation signal.

14. The computer-assisted medical system of claim 1, wherein:

the operations further comprise:

in the pairing mode, receiving the first signal generated by the user input system;

associating the first manipulator with the portion of the user input system further comprises:

associating the first manipulator with the portion of the user input system in response to receiving the first signal generated by the user input system.

15. The computer-assisted medical system of claim 1, wherein:

associating the first manipulator with the portion of the user input system comprises: storing data indicative of an association between the first manipulator and the portion of the user input system; and controlling motion of the first manipulator comprises accessing the stored data.

16. A method of operating a computer-assisted medical system comprising a plurality of manipulators, the method comprising;
 initiating a pairing mode;
 in the pairing mode, associating a first manipulator of the plurality of manipulators with a portion of a user input system based on a first indication generated by the user input system and indicative of movement of the portion of the user input system relative to the first manipulator;
 initiating a following mode; and
 in the following mode, controlling motion of the first manipulator in accordance with a second indication generated by the user input system in response to operation of the portion of the user input system by a user, the second indication being distinct from the first indication.

17. The method of claim 16, wherein associating the first manipulator of the plurality of manipulators with the portion of a user input system based on the movement of the portion of the user input system relative to the first manipulator comprises:
 providing feedback indicative of a proposed association between the portion of the user input system and the first manipulator in response to the movement of the portion of the user input system relative to the first manipulator, and then
 associating the first manipulator with the portion of the user input system in response to receiving a signal indicative of a user confirmation of the proposed association.

18. The method of claim 16, wherein associating the first manipulator of the plurality of manipulators with the portion of a user input system based on the movement of the portion of the user input system relative to the first manipulator comprises:
 associating the first manipulator with the portion of the user input system in response to movement of the portion of the user input system to a region within a predefined distance from the first manipulator, in response to contact between the portion of the user input system and the first manipulator, or in response to a sensor system indicating motion of the portion of the user input system toward a first region defined by a location of the first manipulator.

19. The method of claim 16, further comprising:
 initiating the following mode after associating the first manipulator of the plurality of manipulators with the portion of a user input system and after an orientation of the portion of the user input system is aligned with an orientation of the first manipulator.

20. The method of claim 16, wherein associating the first manipulator of the plurality of manipulators with the portion of a user input system based on the movement of the portion of the user input system relative to the first manipulator comprises:
 associating the first manipulator with the portion of the user input system only if the portion of the user input system is in an unassociated state, or
 associating the first manipulator with the portion of the user input system only if another of the plurality of manipulators is not associated with the portion of the user input system.

21. The method of claim 16, wherein the user input system comprises a plurality of user input devices, the method further comprising:
 guiding association of the first manipulator with the portion of the user input system based on positions or orientations of the plurality of manipulators relative to the plurality of user input devices.

22. One or more non-transitory computer readable media storing instructions that are executable by a processing device, and upon such execution cause the processing device to perform operations comprising:
 initiating a pairing mode;
 associating, in the pairing mode, a first manipulator of a plurality of manipulators with a portion of a user input system based on a first indication generated by the user input system and indicative of movement of the portion of the user input system relative to the first manipulator;
 initiating a following mode; and
 controlling motion, in the following mode, of the first manipulator in accordance with a second indication generated by the user input system in response to operation of the portion of the user input system by a user, the second indication being distinct from the first indication.

23. The one or more non-transitory computer readable media of claim 22, wherein associating the first manipulator of the plurality of manipulators with the portion of a user input system based on the movement of the portion of the user input system relative to the first manipulator comprises:
 providing feedback indicative of a proposed association between the portion of the user input system and the first manipulator in response to the movement of the portion of the user input system relative to the first manipulator, and then
 associating the first manipulator with the portion of the user input system in response to receiving a signal indicative of a user confirmation of the proposed association.

24. The one or more non-transitory computer readable media of claim 22, wherein associating the first manipulator of the plurality of manipulators with the portion of a user input system based on the movement of the portion of the user input system relative to the first manipulator comprises:
 associating the first manipulator with the portion of the user input system in response to movement of the portion of the user input system to a region within a predefined distance from the first manipulator; or
 associating the first manipulator with the portion of the user input system in response to contact between the portion of the user input system and the first manipulator; or
 associating the first manipulator with the portion of the user input system in response to a sensor system indicating motion of the portion of the user input system toward a first region defined by a location of the first manipulator.

25. The one or more non-transitory computer readable media of claim 22, wherein the operations further comprise:
 initiating the following mode after associating the first manipulator of the plurality of manipulators with the portion of a user input system and after an orientation of the portion of the user input system is aligned with an orientation of the first manipulator.

26. The one or more non-transitory computer readable media of claim 22, wherein the user input system comprises a plurality of user input devices, the operations further comprising:
  guiding association of the first manipulator with the portion of the user input system based on positions or orientations of the plurality of manipulators relative to the plurality of user input devices.

* * * * *